(12) United States Patent
Flaherty et al.

(10) Patent No.: US 6,375,615 B1
(45) Date of Patent: Apr. 23, 2002

(54) TISSUE PENETRATING CATHETERS HAVING INTEGRAL IMAGING TRANSDUCERS AND THEIR METHODS OF USE

(75) Inventors: J. Christopher Flaherty, Los Altos; Jason B. Whitt, San Francisco; John Y. Chang, Mountain View; David R. Tholfsen, San Francisco; Philip C. Evard, Palo Alto; Joshua Makower, Los Altos, all of CA (US)

(73) Assignee: TransVascular, Inc., Menlo Park, CA (US)

( * ) Notice: Subject to any disclaimer, the term of this patent is extended or adjusted under 35 U.S.C. 154(b) by 0 days.

(21) Appl. No.: 09/282,774

(22) Filed: Mar. 31, 1999

Related U.S. Application Data

(63) Continuation-in-part of application No. 08/837,294, filed on Apr. 11, 1997, which is a continuation-in-part of application No. 08/730,327, filed on Oct. 11, 1996, now abandoned, which is a continuation-in-part of application No. 08/730,496, filed on Oct. 11, 1996, now Pat. No. 5,830,222.
(60) Provisional application No. 60/080,196, filed on Mar. 31, 1998, provisional application No. 60/010,613, filed on Feb. 2, 1996, and provisional application No. 60/005,164, filed on Oct. 13, 1995.

(51) Int. Cl.$^7$ .................................................. A61B 8/12
(52) U.S. Cl. ........................ 600/439; 604/529; 600/463
(58) Field of Search .................... 600/443, 462–463, 600/466–467, 471; 604/529; 607/122; 606/159, 169–171

(56) References Cited

U.S. PATENT DOCUMENTS

| 4,917,097 A | * | 4/1990 | Proudian et al. | 600/463 |
|---|---|---|---|---|
| 4,950,267 A | | 8/1990 | Ishihara et al. | |
| 5,000,185 A | * | 3/1991 | Yock | 600/466 |
| 5,054,492 A | * | 10/1991 | Scribner et al. | 600/463 |
| 5,437,282 A | | 8/1995 | Koger et al. | |
| 5,438,997 A | | 8/1995 | Sieben et al. | |
| 5,445,155 A | * | 8/1995 | Sieben | 600/443 |
| 5,588,437 A | * | 12/1996 | Crowley | 600/471 |
| 5,596,990 A | | 1/1997 | Yock et al. | |
| 5,676,151 A | | 10/1997 | Yock | |
| 5,699,806 A | | 12/1997 | Webb et al. | |
| 5,713,363 A | * | 2/1998 | Seward et al. | 600/467 |
| 5,715,825 A | * | 2/1998 | Crowley | 600/467 |
| 5,724,977 A | * | 3/1998 | Yock et al. | 600/467 |
| 5,752,518 A | * | 5/1998 | McGee et al. | 600/466 |
| 5,830,222 A | | 11/1998 | Makower | |

OTHER PUBLICATIONS

U.S. application No. 08/730,327, filed Oct. 1996.
U.S. application No. 08/837,294, filed Apr. 1997.

* cited by examiner

Primary Examiner—Francis J. Jaworski
(74) Attorney, Agent, or Firm—Robert D. Buyan; Stout, Uxa, Buyan & Mullins LLP

(57) ABSTRACT

A catheter device that is useable to penetrate from a blood vessel in which the catheter device is positioned to a target location comprises a flexible catheter advanceable into the first blood vessel, a tissue penetrator lumen adapted to receive an operative tissue penetrator which is usable to penetrate from the blood vessel to the target location when properly aimed. Further said catheter including an imaging transducer fixedly mounted on or within the catheter body to provide an imaging signal from which an image of the target location can be obtained. The catheter device may include an imageable marker on the catheter to form on the image obtainable from the imaging signal a penetrator path indication that indicates the path that will be followed by the tissue penetrator when the tissue penetrator exits from the catheter. Alternatively, or addition thereto, the imaging transducer may comprise a plurality of imaging elements which are located so that the penetrator path indication can be obtained. A method of utilizing such a catheter device to bypass an arterial obstruction is also disclosed.

35 Claims, 14 Drawing Sheets

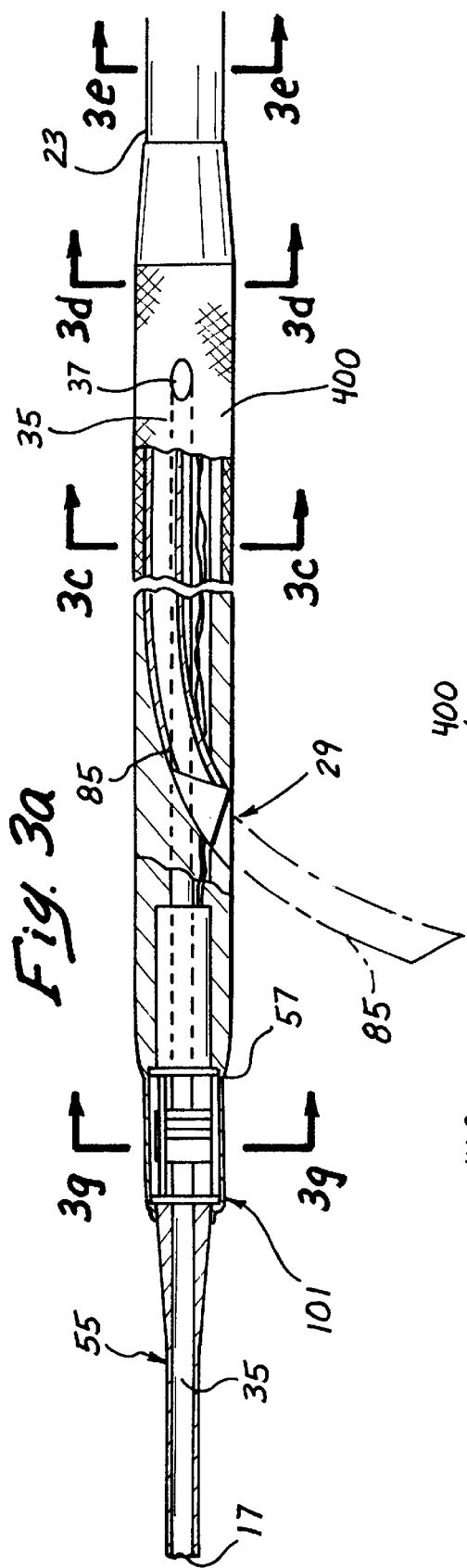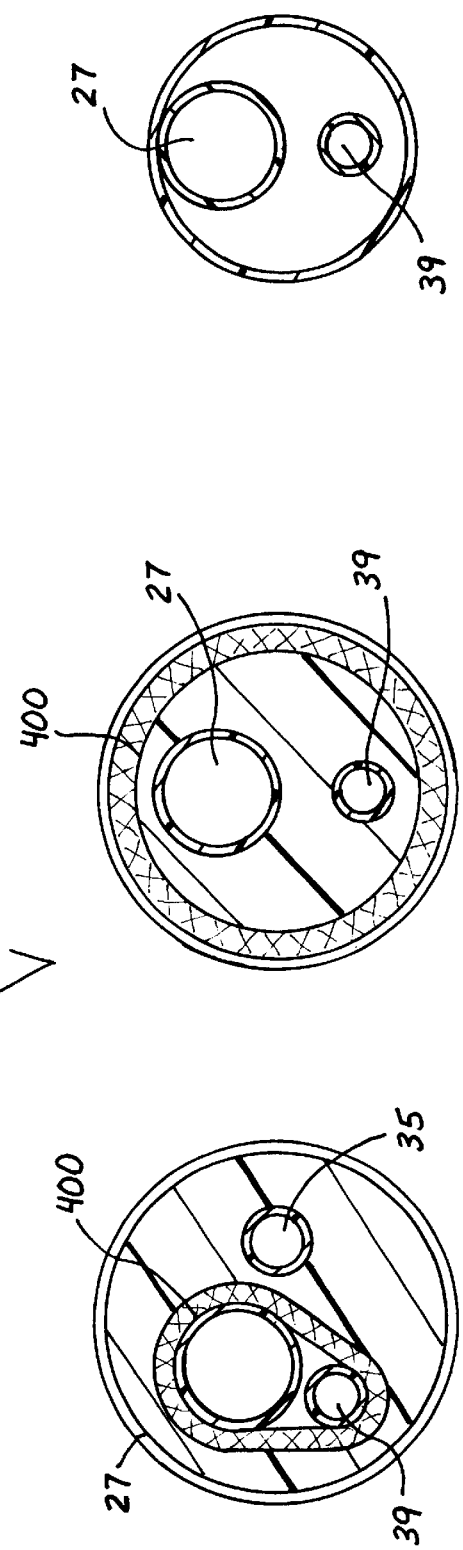

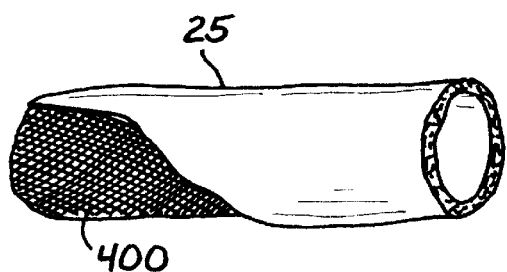
Fig. 3a'
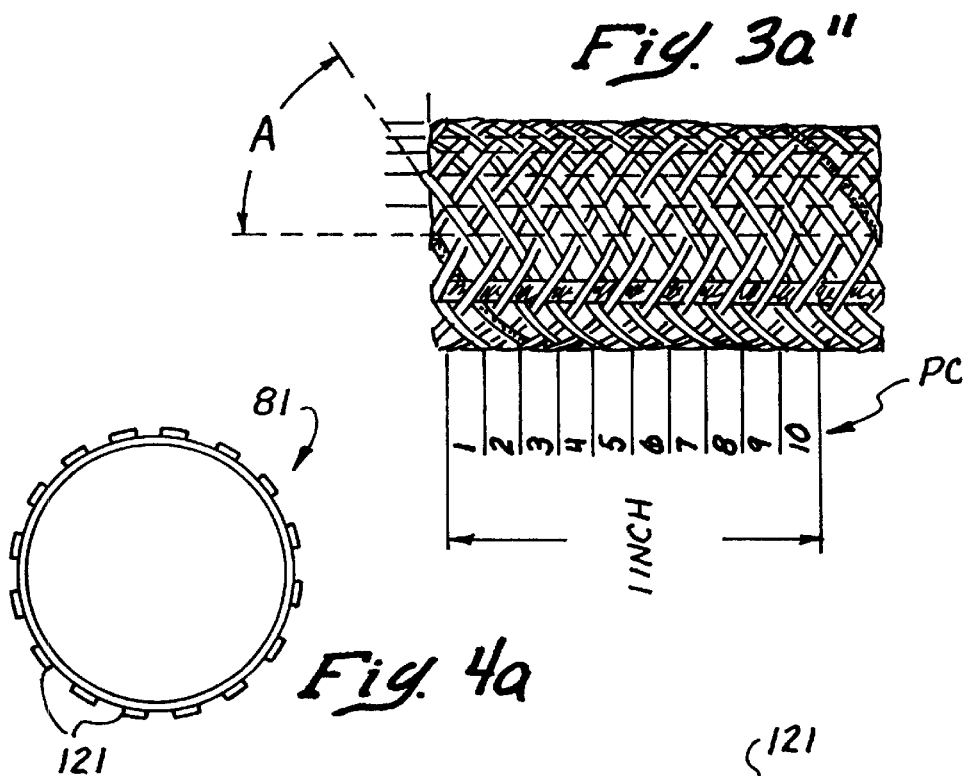
Fig. 3a"
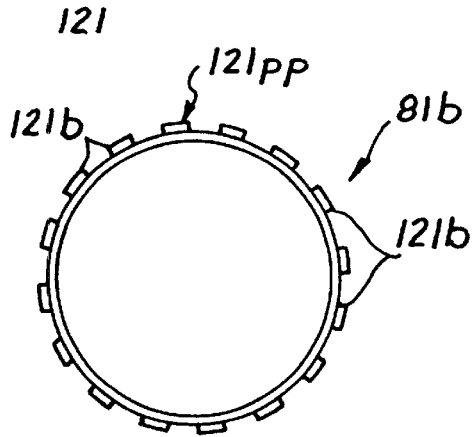
Fig. 4a
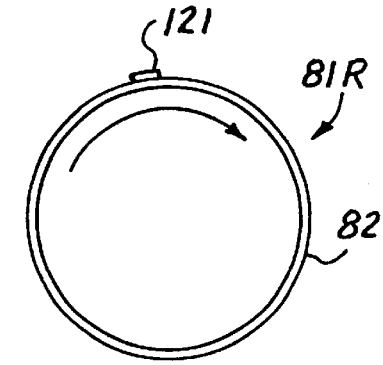
Fig. 4b
Fig. 4a'

TISSUE PENETRATING CATHETERS HAVING INTEGRAL IMAGING TRANSDUCERS AND THEIR METHODS OF USE

RELATED APPLICATION

This application claims priority to United States Provisional Application No. 60/080,196 filed Mar. 31, 1998 and is a continuation-in-part of U.S. patent application Ser. No. 08/837,294 filed on Apr. 11, 1997, which itself is a continuation-in-part of two-earlier filed applications, namely; U.S. patent application Ser. No. 08/730,327 filed Oct. 11, 1996 and 08/730,496 now U.S. Pat. No. 5,830,222, both of which were filed on Oct. 11, 1996 and both of which claim priority to earlier-filed U.S. Provisional Patent Application Nos. 06/005,164 filed Oct. 13, 1995 and 60/010,613 filed Feb. 2, 1996, the entire disclosures of all such related applications being expressly incorporated herein by reference.

FIELD OF THE INVENTION

The present invention relates generally to medical devices and methods, and more particularly to catheter devices and methods that are useable to form channels (e.g., penetration tracts) between vessels such as arteries and veins and vessels and other anatomical structures, in furtherance of a therapeutic purpose such as bypassing an arterial blockage, delivering therapuetic agents, or performing other interventional procedures.

BACKGROUND OF THE INVENTION

Atherosclerotic cardiovascular disease remains a major cause of premature death and morbidity, in most regions of the world. Various transluminal, catheter-based interventional techniques have been used, or proposed for use, to dilate or otherwise treat atherosclerotic obstructions that occur in coronary and/or peripheral arteries. These therapies have traditionally focused on treating the disease intraluminally, or from "within" the vessel lumen.

Included among the newer interventional techniques are certain percutaneous, transluminal techniques for bypassing obstructions in coronary or peripheral arteries through the use of the adjacent vein(s) as in situ bypass conduit(s); (e.g. using catheters to perform extra luminal procedures outside the diseased vessel lumen. These procedures are described in U.S. Pat. No. 5,830,222 (Makower) and in published PCT Applications WO 98/16161 and WO 98/46119. As described therein, in some instances, these procedures may be performed by a venous approach wherein a tissue penetrating catheter is inserted into a vein and the desired passageway or puncture is initially formed by facilitating the passage of a tissue penetrator (e.g., a flow of energy or an elongate penetration member) from a catheter, through the wall of the vein in which the catheter is positioned, and into a target location such as the lumen of an adjacent vessel (e.g. the artery). Alternatively, some of these procedures may be performed by an arterial approach wherein the catheter is inserted into an artery and the desired passageway or puncture is initially formed by facilitating the passage of a tissue penetrator (e.g., a flow of energy or elongate penetration member) from the catheter, through the wall of the artery in which the catheter is positioned, and into the target location such as the lumen of an adjacent vessel (e.g. a vein). It is typically necessary for the tissue-penetrating catheter to be placed in proper rotational orientation within the blood vessel, prior to facilitating the passage of the tissue penetrator therefrom, to ensure that the tissue penetrator is aimed or positioned to enter the target. To facilitate such aiming of the tissue penetrator, some of the previously described tissue penetrating catheters have included a penetrator direction marker that indicates the direction in which the tissue penetrator will pass from the catheter and an imaging catheter lumen through which a separate intravascular ultrasound imaging catheter (IVUS catheter) can be advanced. After the separate IVUS catheter has been advanced into the imaging lumen of the tissue penetrating catheter, the IVUS is used to image the target and the penetrator direction marker. The catheter can then be rotated within the blood vessel until the penetrator direction marker is aligned with the target, thereby indicating that subsequent advancement of the tissue penetrator from the catheter will result in the formation of the desired penetration tract between the blood vessel in which the catheter is positioned and the target.

Applicant has determined that, in cases where the tissue-penetrating catheter is to be placed in a relatively small blood vessel such as branches of the coronary artery, carotid arteries, or smaller vessels located in the peripheral vasculature (e.g. vessels in the arms or legs), it is desirable for the tissue penetrating catheter to be of reduced profile while still having sufficient column strength and torque transfer properties to allow the operator to rotate and maneuver the distal end of the catheter within the patients body by twisting, pushing and pulling the proximal end of the catheter that remains outside of the patient's body. Thus, because the provision of a separate imaging catheter lumen substantially increases the required diameter of the tissue penetrating catheter, it is desirable to devise new tissue penetrating catheter designs that do not include an imaging catheter lumen while still maintaining the capability of imaging from a vantage point near the catheter's distal end to facilitate proper rotational orientation of the tissue penetrating catheter to facilitate aiming of the tissue penetrator.

SUMMARY OF THE INVENTION

This invention facilitates accurate and reliable orientation of a tissue penetrating catheter in a blood vessel so that an adjacently located blood vessel or other anatomical target can be accurately penetrated, while eliminating the need for formation of a separate imaging lumen within the tissue penetrating catheter. Thus, because the need for an imaging lumen has been eliminated, the tissue penetrating catheters of this invention may be of reduced profile (e.g., 5–7 French diameter).

In accordance with the invention, there is provided a tissue penetrating catheter device that comprises an elongated catheter having an instrument lumen to facilitate the passage of a tissue penetrator, a penetrator direction marker, and an integral imaging transducer (e.g., an IVUS transducer). To facilitate orientation, the imaging transducer is useable to provide an imaging signal from which an image of the target structure and other adjacent anatomical structures can be obtained. The imaging transducer is fixedly mounted on or within the catheter, thereby eliminating the need for a separate imaging lumen which requires sufficient clearance in the lumen to allow a separate imaging transducer to be advanced and retracted in the lumen. This in turn enables the catheter to be of smaller cross sectional area. In addition, by fixedly mounting the imaging transducer on the catheter, its orientation relative to the catheter and certain components on the catheter can be specifically known.

One advantageous approach to imaging is to employ an imaging transducer which includes a plurality of imaging elements fixedly mounted on the catheter to provide an imaging signal from which an image of adjacent structures can be obtained. The imaging elements are mounted on the catheter at known circumferential locations relative to the path that will be followed by the tissue penetrator as the tissue penetrator exits from the catheter. The image obtained from the imaging signal from the imaging transducer is useable by the operator to rotationally orient the catheter such that, when the tissue penetrator subsequently exits the catheter, the tissue penetrator will extend into the desired target. In addition, the imaging transducer is useable to image other structures to allow several diagnostic functions such as assessing calcification of a vessel, distance of the target location to the vessel in which the catheter is positioned, and the presence of other devices.

Another advantageous approach to imaging is to provide an imaging marker on the catheter to form, on the image obtainable from the imaging signal from the imaging transducer, a penetrator path indication. This penetrator path indication is indicative of the path that will be followed by the tissue penetrator when the tissue penetrator exits from the catheter. The imaging transducer and the marker are useable in cooperation with each other to enable the operator to rotationally orient the catheter until the penetrator path indicator is aimed at the target thereby indicating that when the tissue penetrator exits from the catheter it will extend to the target as desired. The imaging elements fixedly mounted on the catheter at known circumferential locations can also be used to orient the catheter without any imageable markers.

When an imageable marker is used, it preferably includes a structure formed on the catheter including at least one longitudinal member disposed circumferentially about a hollow interior space. When a plurality of longitudinal members is employed, said longitudinal members are disposed at circumferentially spaced apart locations about a hollow interior space thereby forming a cage. At least one of such longitudinal members is located at a circumferential position that is axially aligned with the path or plane of the path that will be followed by the tissue penetrator as it exits from the catheter.

The tissue penetrator may be any instrument for penetrating the target of interest. For example, the tissue penetrator may be or include a laser beam, flow of energy, or an instrument which will itself puncture or penetrate the target of interest. One preferred form of tissue penetrator includes a needle member formed of resilient material that is biased to a preformed curved configuration with the needle member being initially disposed in a retracted position within the catheter and subsequently advanceable from the catheter to an extended position wherein the needle member assumes its preformed curved configuration.

The imaging transducer of the current invention is preferably an ultrasound imaging transducer and more preferably a phased array transducer. Because the phased array transducer can be fixed in a permanent manner on or within the catheter body, said phased array transducer has the advantage of being useable with or with out an imageable marker to obtain reliable and accurate orientation. Moreover, the nature of the imaging elements and the fact the imaging signal can be transmitted by multiplexing numerous signals on fewer lead wires contribute to the small profile of the catheter.

The catheter may include an elongated catheter body having a proximal end, a distal end and a peripheral wall with at least a distal region of the catheter body being flexible enough to navigate through the coronary vessels. The catheter body has an penetrator lumen that terminates distally at an exit location on the peripheral wall and contains or is adapted to receive an instrument or other tissue penetrator for penetrating the blood vessel in which the catheter body is received ("resident blood vessel") to a target adjacent to the resident blood vessel. The phased array transducer is preferably an onboard transducer which is mounted on or within the catheter body and is inseparable or not removable from the catheter body. The phased array transducer is carried by the catheter body in fixed relationship to the catheter body and in some instances, in a known orientation relative to the exit location. The phased array transducer provides an imaging signal for use in locating the target and identifying the angular orientation of the exit location. Accordingly, with the penetrator received in the penetrator lumen the catheter body can be rotated to properly orient the exit location so that the penetrator can penetrate the resident blood vessel into which the catheter body is receivable and into the target. The catheter body is of sufficiently small profile so that it can be received within a coronary artery, branch or peripheral vessel if desired.

The catheter may be considered as including an imageable marker which may include a plurality of circumferentially spaced imageable members carried by the catheter body in a known circumferential orientation relative to the exit location. The imageable markers can be sensed by the phased array transducer and used to locate the target and in identifying the angular orientation of the exit location.

The phased array transducer may comprise a plurality of imaging elements arranged on the catheter body with at least one of the elements being at a known circumferential location relative to the exit location so that such at least one element is useable to identify the angular orientation of the exit location. Alternatively or in addition thereto, the at least one element may form an image region that defines an acceptable zone of penetration for the tissue penetrator.

In a preferred construction, the catheter body includes a major section which includes a proximal end and the exit location and a distal tip section extending from the major section to the distal end. The distal portion of the distal tip section has a smaller cross sectional area than the adjacent region of the major section. An active imaging apparatus is carried by the catheter body and includes imaging elements fixedly mounted on the distal tip section and a lead or leads extending proximally from the imaging elements along the catheter body. Accordingly, the reduced diameter portions of the catheter body are used to mount the imaging elements, to thereby minimize the profile of the catheter at this region of the catheter. Although various constructions are possible, in one preferred form of the invention, the major section terminates distally in a distal opening and a proximal portion of the distal tip section is received in the distal opening and a distal portion of the distal tip section extends distally of the distal opening.

The method of this invention includes inserting and transluminally advancing the catheter of this invention into a first blood vessel, actuating the imaging transducer and moving the catheter within the first blood vessel until the penetrator path indication is aimed at the target, and thereafter facilitating the exit of the tissue penetrator from the catheter through the wall of the first blood vessels and into the target. Thereafter various procedures may be performed such as the delivery of therapeutic agents or diagnostic devices.

In procedures where it may be advantageous to perform subsequent procedures over a guidewire, such as the formation of passageways between a first blood vessel and a target, the method may also include advancing a first crossing guidewire through the lumen of the tissue penetrator and into the target, such as the lumen of the second blood vessel or other target and retracting the tissue penetrator into the catheter leaving the first crossing guidewire in place.

In some procedures, such as those novel procedures more fully described in U.S. Pat. No. 5,830,222 and in U.S. patent applications Ser. Nos. 08/730,496, 09/048,147 and 09/048, 147, and other means of revascularizing oxygen starved tissues or delivering therapuetic substances to vessels, tissue and other organs, it may be advantageous to obtain a second point of access to the same vessel into which the catheter was initially introduced at some point distal of the first crossing. However, this access may be limited due to the presence of calcium or other vessel disease blocking the lumen of the vessel. To obtain catheter access to a second point, distal of a diseased section in the same blood vessel, the first crossing guidewire is removed from the lumen of the tissue penetrator and reintroduced into the main guidewire lumen of the catheter and the catheter may be readvanced over the first crossing guidewire to a position wherein the catheter extends through the lumen of the first blood vessel, and through the openings created in the walls of the first and a second blood vessel. Thereafter, the catheter can be advanced distally in the lumen of the second blood vessel. To gain access back to the first blood vessel at a different location (e.g. past the disease or obstruction), the imaging transducer is actuated and the catheter is moved within the second blood vessel as required to cause the penetrator path indication to be aligned with the lumen of the first blood vessel. The tissue penetrator is advanced from the catheter through the wall of the second blood vessel and through the wall and into the lumen of the first blood vessel. To obtain guidewire access to the first blood vessel, a second crossing guidewire is advanced through the lumen of the tissue penetrator and into the lumen of the first blood vessel. The tissue penetrator is retracted into the catheter leaving the second crossing guidewire in place such that it extends from the lumen of the first blood vessel into the lumen of the second blood vessel and back into the lumen of the first blood vessel.

As part of the invention envisioned herein, a radial expandable connector can be used to provide a blood flow passageway between the blood vessels. For example, a connector delivery catheter can be advanced over the second crossing guidewire and the connector implanted such that the connector extends from the lumen of the first blood vessel through the openings created in the walls of the first and second blood vessels through the lumen of the second blood vessel through the openings created in the walls of the first and second blood vessels and back into the lumen of the first blood vessel.

The invention together with additional features and advantages thereof may best be understood by reference to the following description taken in connection with the accompanying illustrated drawings.

BRIEF DESCRIPTION OF THE DRAWINGS

FIG. 3a is an enlarged fragmentary elevational view partially in section showing a distal portion of the catheter.

FIG. 3a' is an enlarged, cut-away view of the wire braid formed within the distal section of the catheter body.

FIG. 3a" is a diagram of a catheter braid illustrating the braid angle and pick count of the braid.

FIGS. 3c, 3d and 3e are cross sectional views taken generally along lines 3c—3c, 3d—3d, and 3e—3e of FIG. 3 respectively.

FIG. 3g is a cross sectional view through FIG. 3g—3g of FIG. 3a.

FIGS. 4a and 4a' are schematic diagrams of a annular phased array transducers that may ne mounted within catheters of the present invention.

FIG. 4b is a schematic diagram of an alternative single element transducer that is rotatable within or in conjunction with the catheter.

DETAILED DESCRIPTION OF PREFERRED EMBODIMENTS

Set forth herebelow are detailed descriptions of certain embodiments and examples of the catheter devices and methods of the present invention.

Figure 1:
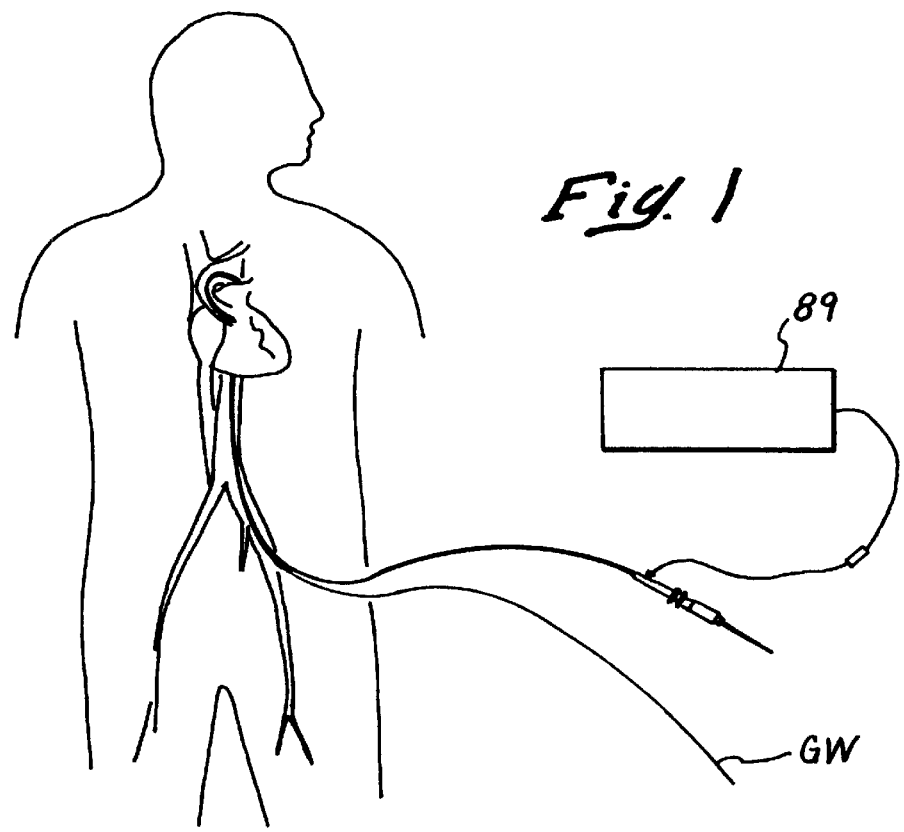
FIG. 1 is schematic illustration showing the catheter of this invention in use on a human patient.
Figure 2:
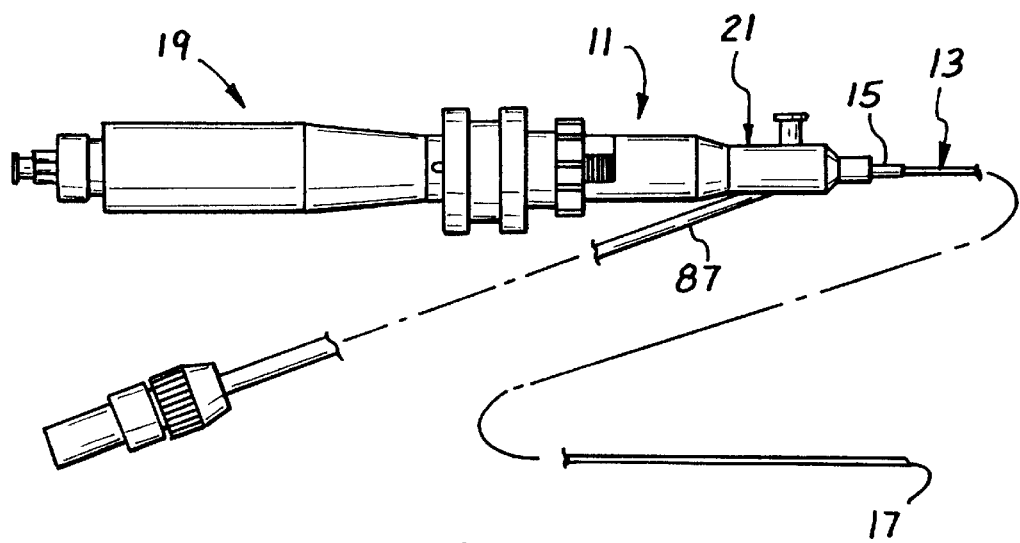
FIG. 2 is an elevational view of one form of catheter constructed in accordance with the teachings of this invention.

First Embodiment: Catheter With Phased Array (or Rotatable) Imaging Transducer and Marker Structure For Indicating Penetrator Path FIG. 2 shows a catheter 11 constructed in accordance with the teachings of this invention, while FIG. 1 shows the catheter 11 in use on a human patient. In the embodiment illustrated, the catheter 11 includes an elongated catheter body 13 having a proximal end 15, a distal end 17, a handle 19 and a hub 21 coupled to the proximal end of the catheter body 15 and to the handle. The handle 19 may also serve as a controller for use in advancing and retracting the penetrating instrument, such as a tissue penetrator 85 described more fully below.

The Catheter Body

The catheter body 13 includes a relatively rigid proximal section 23 shown in FIGS. 2 and 3a which may be constructed, for example, of a metal hypo tube and an elongated flexible distal section or region 25 suitably joined to the proximal section. A hand piece 19 is attached to the proximal end of the proximal section 23, as shown. In the preferred embodiment the hand piece 19 and proximal section 23 are approximately 100 cm in length. The flexible distal section 25 may incorporate a reinforcement member such as a wire braid 400 as shown in FIGS. 3a and 3a' and, in the preferred embodiment is approximately 30 cm in length. The braid 400 terminates approximately 3 cm from the distal end 17.

It has been determined that material expansion and changes in the physical properties of certain materials may occur after the catheter 11 is inserted into the patient's body and warmed from room temperature to body temperature. This material expansion and changes in the physical properties of certain materials can result in variation in the tolerances and sizing of the catheter 11 (e.g. elongation or shrinking) and can thus give rise to an unwanted modification of the position of the tissue penetrating member 85. This could, in at least some cases, interfere with the precise aiming and advancement of the tissue penetrating member as desired. FIG. 3a" illustrates the braid angle A and pick count PC of the catheter braid 400. The "pick count" PC of the braid is, as is well known in the art, a function of the braid angle A (i.e., the greater the braid angle the more picks per inch). Also, the torque transmission and stiffness of the braided distal section 25 is a function of the braid angle (i.e., a braid angle of 90 degrees provides maximum torque transfer and a braid angle of 0 degrees provides minimum torque transfer). Typically, cardiovascular catheters used in procedures such as those described herein utilizing a venous approach have braid angles A that result in a pick count of 50–70 picks per inch. However, applicant has determined that by decreasing the braid angle A of the braid 400 within the distal section 25 of the catheter 11 to result in a lower pick count, it is possible to minimize or eliminate the unwanted longitudinal expansion of the catheter 11 and/or its components, while retaining sufficient torque transmission and acceptable stiffness to accomplish the procedures for which the catheter 11 is intended (examples of such procedures are illustrated in FIGS. 7a–8d herebelow). This variation in braid angle or picks per inch may vary depending on the material of construction of the catheter and/or the braid fiber, and the diameter of the catheter body.

In instances where the catheter 11 is intended for use in a coronary artery, at least the distal section 25 of the catheter 11 is sized to be received within a coronary artery, and therefore can be received within either a coronary artery or a coronary vein or other lumens of equal diameter. The catheter body section 13 has a penetrator lumen 27 that terminates distally at an exit location or exit port 29 (FIG. 3a) on a peripheral wall 31 of the catheter body. The penetrator lumen 27 extends proximally from the exit port 29 to the proximal end 15 of the catheter body 13 and communicates with the interior of the handle 19 through the hub 21. The penetrator lumen 27 contains or is adapted to receive an instrument, such as the tissue penetrator 85 shown in FIG. 3a, for penetrating out of the blood vessel in which the catheter 11 resides (i.e., the "resident vessel") and to a target location. The exit port 29 is preferably located a short distance proximally of the distal end 17. A radiopaque marker 33 is mounted on the lumen 27 adjacent the exit port 29.

The catheter body 13 also has a guidewire lumen 35 (FIG. 3a) which extends to the distal end 17 of the catheter body 15. In this embodiment, the guidewire lumen 35 extends proximally to an inlet port 37 at the peripheral wall 31 closely adjacent the proximal section 23. The catheter body also has a lead lumen 39 (FIG. 3c) for a purpose described below.

Figure 3B:
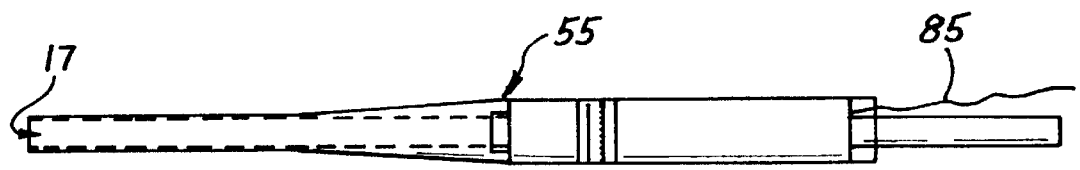
FIG. 3b is an enlarged elevational view showing the distal tip section of the catheter.

A major section 51 of the catheter body 13 terminates distally in a distal opening 53, and the catheter body includes a distal tip section 55 of soft, flexible, biocompatible material (FIGS. 3a and 3b). A proximal portion 56 of the distal tip section 55 is received in the distal opening 53 and a distal portion of the distal tip section extends distally to the distal end 17. The distal portion of the distal tip section 55, i.e. the portion of the distal tip section 55 which extends beyond the distal end of the major section 51 is of smaller cross sectional area than the adjacent region of the major section to thereby define an annular shoulder 57 on the catheter body 13. The exit port 29 is spaced slightly proximally of the shoulder 57.

Phased Array Transducer

An imaging transducer 81 is fixedly mounted on the catheter 11, and in the embodiment illustrated in FIG. 3a, the imaging transducer is mounted on the distal tip section 55 just distally of the shoulder 57. In this embodiment, the imaging transducer 81 is a phased array transducer of the type shown schematically in FIG. 4a and is operative to image 360° about the catheter 11. This imaging transducer 81 comprises an annular array of individual crystals or elements 121 is coupled to a multiplex circuit 83 which is within the major section 51 of the catheter body 13 adjacent the shoulder 57, and the multiplex circuit 83 is in turn coupled to leads 85 which extend through the lead lumen 39 and a port 87 (FIG. 2) of the hub 21 to an imaging console 89. When activated, the imaging transducer emits ultrasound signals and receives back echos or reflections which are representative of the nature of the surrounding environment. The imaging transducer provides an imaging signal from which an image of the surrounding structure can be created by signal processing apparatus located in the imaging console 89 and viewed on a standard display screen located near the operating table on which the patient is positioned. In a preferred practice of this invention, the phased array transducer and the accompanying circuitry and the imaging console 89 may be obtained from Endosonics of Rancho Cordova, Calif. or Intravascular Research Limited (United Kingdom).

Alternative Rotatable Transducer

In an alternate embodiment of this invention, a rotatable imaging transducer 81r of the type illustrated schematically in FIG. 4b may be used. This alternative transducer 81r comprises one (or more than one) imaging element 121r that is mounted on a rotating shaft 82 that extends through a portion of the catheter body (e.g., and out of port 39) such that it can be rotated relative to the catheter body. Alternatively, it will be appreciated that this transducer 81r may be fixedly mounted within or upon the catheter body and the entire catheter body may be rotated in order to effect rotational movement of the transducer element 121r.

Marker Structure

Figure 3F:
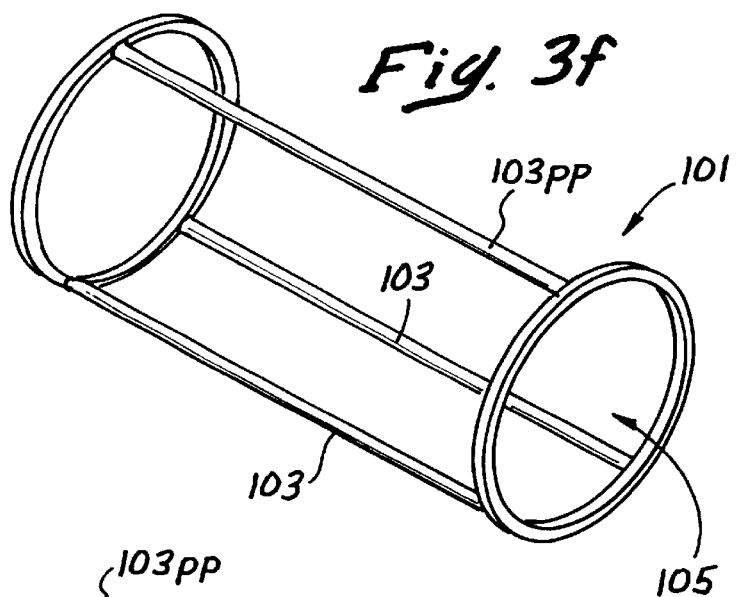
FIG. 3f is a perspective view of the marker structure of the catheter embodiment shown in FIGS. 3a–3b.
Figure 3G:
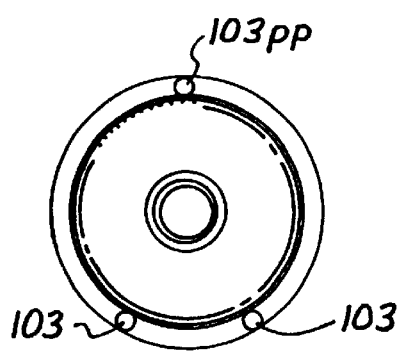

In this first embodiment (FIGS. 3a–3e), an imageable marker structure 101 is fixedly mounted on the catheter body 13 in a known circumferential orientation relative to the exit port 29. In the embodiment of FIG. 3a, the marker structure 101 is in the form cage (FIG. 3f) and the transducer 81 is within the cage. This marker structure 101 comprises a plurality of longitudinal members 103 and 103pp disposed at circumferentially spaced apart locations about a hollow interior space 105. The hollow space 105 receives the distal tip section 55 and the transducer 81, and the transducer 81 is an onboard transducer in that it is inseparable from and not removable from the catheter body 13. In this embodiment the transducer 81 is attached to or wrapped around the catheter body 13 and permanently retained by a suitable potting composition or adhesive. As shown in FIG. 3g, one of the longitudinal members 103pp is designated as the penetrator path indicating member and is positioned at a circumferential position that is axially aligned with the exit port 29 or otherwise positioned to be indicative of the path that will be followed by the tissue penetrator 85 as it is advanced from the catheter body 13 through the exit port 29. Thus, the imageable marker structure 101 forms on the image obtainable from the imaging signal from the imaging transducer a penetrator path indication that indicates the path that will be followed by the tissue penetrator when the tissue penetrator 85 exits from the catheter.

With the construction described above, the imaging transducer 81 and the marker 101 are both mounted on the distal tip section 55 which has a smaller cross sectional area than does the adjacent region of the major section 51 of the catheter body 13. Accordingly, the cross sectional area of the catheter body 13 at the region containing the imaging transducer 81 and the marker 101 can still be relatively small. Also, the exit location 29 is closely adjacent to the imaging transducer 81 and may be, for example, about 3 mm from the imaging transducer. This minimizes the likelihood of any significant torsional displacement of the exit location 29 relative to the marker 101 and imaging transducer 89. It may also be appreciated that the imaging transducer may be mounted such that the exit port is located directly at the point at which the transducer is affixed to the catheter, eliminating any displacement.

Figure 6B:
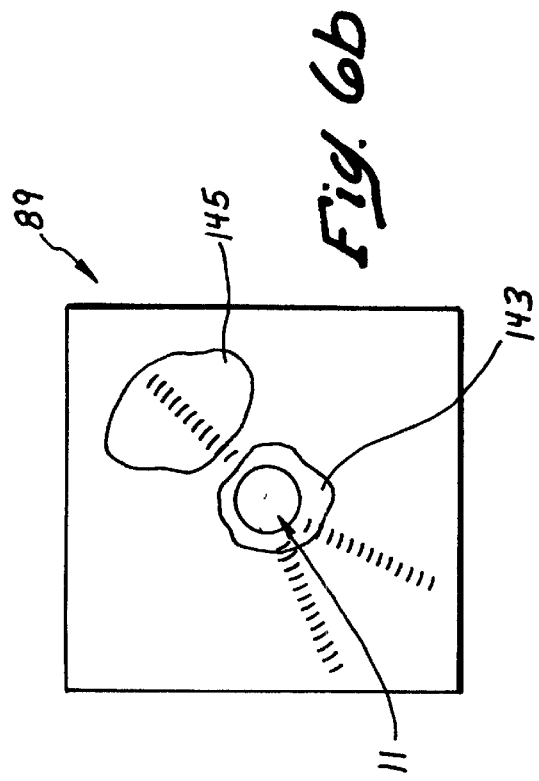
FIGS. 6a and 6b are views similar to FIGS. 5a and 5b respectively illustrating how the catheter embodiment of FIG. 3a can be rotationally oriented within the blood vessel to cause the image created by the penetrator-path-indicating member of the marker structure (i.e., the particular strut member of the marker structure that is aligned with the path that will be followed by the tissue penetrator when the penetrator is advanced from the catheter body) to be aimed at the target location to which the penetrator is intended to travel.
Figure 6A:
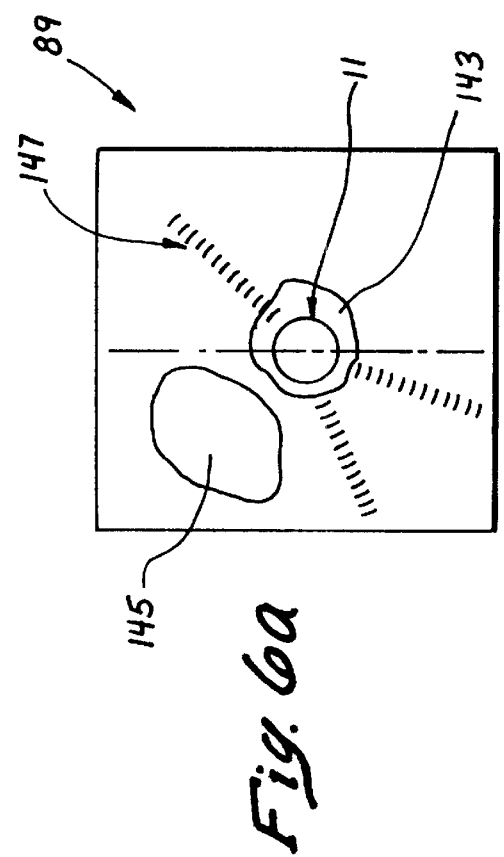

FIGS. 6a and 6b show an image of what the operator sees on the display screen of the imaging console 89 when the catheter 11 is advanced into the resident blood vessel. Specifically, FIG. 6a shows an image of the catheter 11, an image 143 of the resident blood vessel into which the catheter 11 has been inserted (i.e., the blood vessel in which the catheter 11 resides) and an image of a target blood vessel 145 adjacent to the blood vessel 143. In this particular illustration, the blood vessels represented by images 143 and 145 are a coronary artery and coronary vein, respectively. In FIG. 6a, the image created by the penetrator-path-indicating member 103pp of the marker structure 101, as represented by line or artifact 147, does not extend into the lumen of the target blood vessel 145. Thus, if the tissue penetrator 85 were to be advanced from the catheter 11 while the catheter 11 is in the rotational orientation shown in FIG. 6a, the tissue penetrator would not advance into the lumen of the target blood vessel 145, as desired. However, by rotating the catheter 11 within the resident blood vessel 143, the operator may cause the image created by the penetrator-path-indicating member 103pp of the marker structure 101, as represented by line or artifact 147, to extend into the lumen of the target blood vessel 145 as illustrated in FIG. 6b. Thus, if the tissue penetrator 85 were to be advanced form the catheter 11 while the catheter 11 is in the rotational orientation shown in FIG. 6b, the tissue penetrator 85 would advance into the lumen of the target blood vessel 145, as desired.

Figure 4:
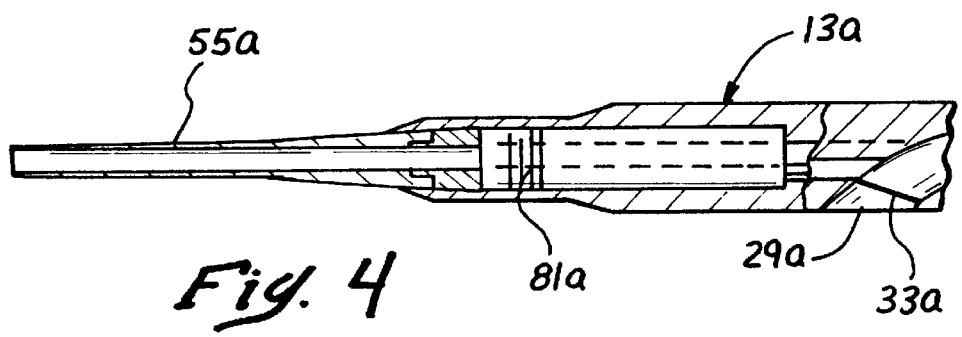
FIG. 4 is an elevational view similar to FIG. 3a illustrating a second embodiment of the catheter.

B. Second Embodiment: Catheter with Fixedly Mounted Imaging Transducer Useable Without Marker Structure FIG. 4 shows a second embodiment of the catheter 11a which is identical to the catheter 11 in all respects not shown or specified as being different herebelow. Portions of the catheter 11a corresponding to portions of the catheter 11 are designated by corresponding reference numerals followed by the letter a.

The primary difference between the catheters 11 and 11a is that the catheter 11a has no imageable marker structure 101. Instead, its imaging transducer 81a is mounted in a fixed position such that one particular element 121pp (or a group of particular elements) is/are designated as the penetrator path but rather is mounted in a fixed orientation within or upon the catheter such that a selected one (or selected ones) of the individual imaging elements 121 (e.g., crystals) of the phased array is positioned in known spacial relation to the path or plane of the path that will be followed by the tissue penetrator as exits from the catheter. This selected one (or ones) of the imaging elements 121 shall be referred to herein as the "penetrator-path-indicating element 121pp." The imaging elements 121, which may be adhered to the catheter body 13a, are mounted on the catheter 11 at known circumferential locations relative to the path that will be followed by a tissue penetrator as the tissue penetrator advances from the catheter 11 through the exit port 29a. The image obtained from the imaging signal from the imaging transducer 81a is thereby useable by the operator to rotationally orient the catheter 11 such that when the tissue penetrator subsequently exits from the catheter, the tissue penetrator will extend into the target as desired. Thus, because the imaging elements 121a are mounted on the catheter body 13 in fixed relationship to the catheter body and in a known circumferential orientation relative to the exit location 29a, the imaging transducer 81a can be used to provide an imaging signal for use in locating an adjacent blood vessel or other structure and identifying the angular orientation of the exit location. If desired, the imaging elements of the imaging transducer 81 of the catheter 11 can be oriented in the same fashion as described above for the catheter 11a. In this event, the only difference between the catheters 11 and 11a would be that the catheter 11 has an imaging marker 101 and the catheter 11a does not.

Figure 5B:
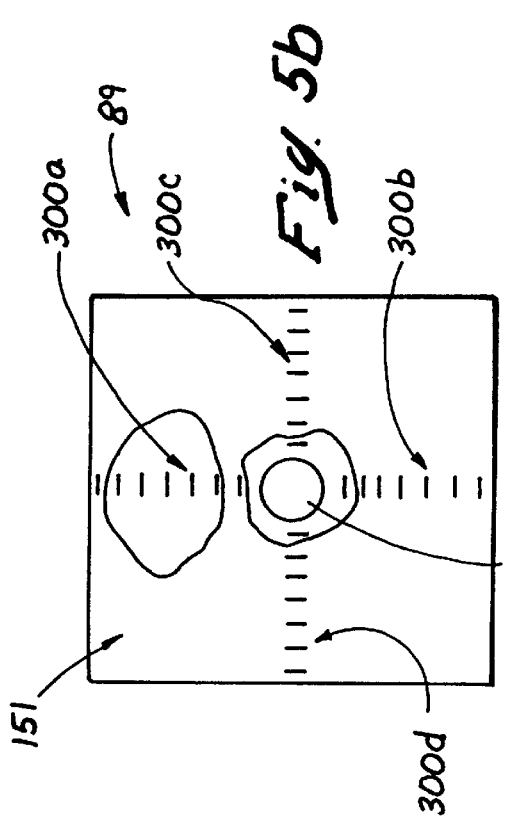
FIGS. 5a and 5b are elevational views of the screen of the imaging apparatus showing standard quadrant-indicating hash marks on the screen, and illustrating the manner in which the fixed-transducer catheter of FIG. 4 can be rotationally oriented within the blood vessel to cause a penetrator-path-indicating element (and hence the penetrator) to become aimed at a target location to which the penetrator is intended to travel.
Figure 5D:
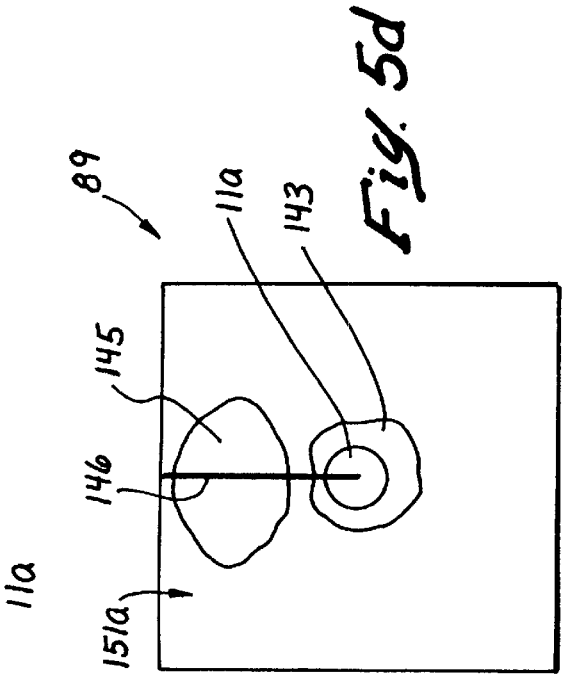
FIGS. 5c and 5d are elevational views of the screen of an imaging apparatus whereon a line has been marked to denote the location of the particular penetrator-path-indicating element of the fixed-transducer catheter of FIG. 4, and illustrating the manner in which the line can be used to facilitate rotational orientation of the catheter within the resident blood vessel such that the penetrator-path-indicating transducer element (and hence the penetrator) are aimed at the target location.
Figure 5A:
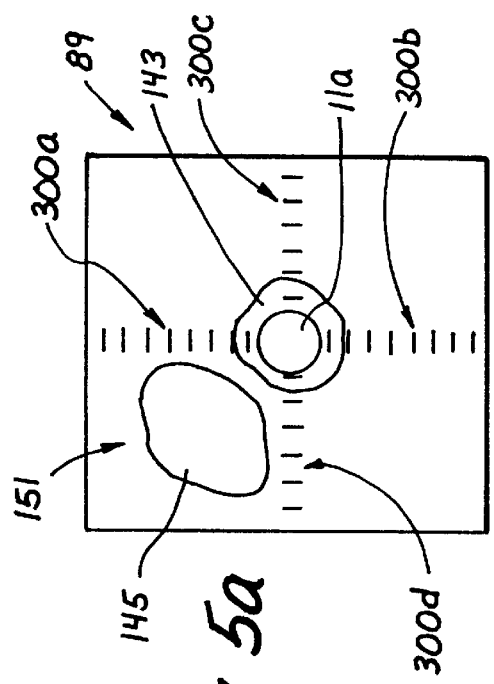

FIG. 5a shows an image 151 of the catheter 11a (FIG. 4) in the resident blood vessel 143 in which that catheter is positioned, as well as an image of the target location 145, shown here as another blood vessel. Standard serial hash marks 300a, 300b, 300c and 300d are formed on the imaging screen as shown, generally dividing the screen into four quadrants. In this instance, the transducer 81b is fixedly mounted within the catheter 11a such that its penetrator path indicating transducer element 121pp is in the 12 o'clock position and aligned with the top array of hash marks 300a on the imaging screen. Thus, the top array of hash marks 300a serve as a visual indicator of the path that will be followed by the tissue penetrator 85 as it is advanced from the catheter 11a. In the showing of FIG. 5a, one can see that the top hash marks 300a do not enter the target location 145 and thus, it can be concluded from this image that the tissue penetrator 85 is not properly aimed at the target location. However, by rotating the catheter 11a in the resident blood vessel 143, to the position shown in FIG. 5b, the top array of hash marks 300a is caused to pass directly through the target location 145, thus indicating to the operator that the tissue penetrator 85 can now be advanced from the exit port 29a to properly penetrate from the resident vessel 143 into the target location 145, as desired.

Figure 5C:
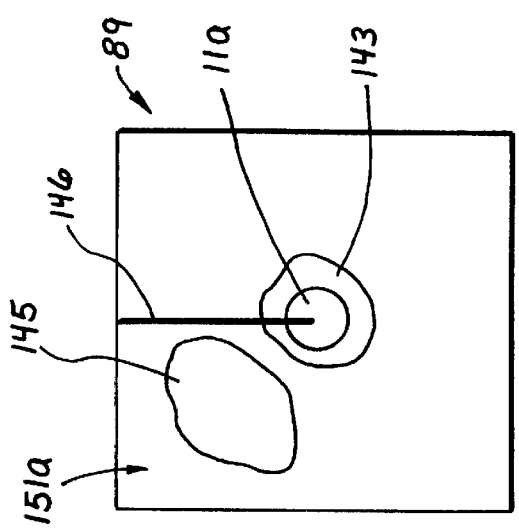

FIGS. 5c and 5d show an image 151a of the catheter 11a (FIG. 4) in the resident blood vessel 143 in which that catheter is positioned, as well as an image of the target location 145, shown here as another blood vessel. A vertical line 146 has been created on the screen 146 in alignment with the position of a penetrator path indicating transducer element 121pp. of the phased array transducer 81b. Thus, the line 146 serves as a visual indicator of the path that will be followed by the tissue penetrator 85 as it is advanced from the catheter 11a. It will be appreciated by those of skill in the art that this line 146 may be created on the imaging screen 89 electronically (e.g., as an illuminated or colored line on the image) or it may be physically marked on the screen 89 (e.g., by felt tipped marker or other suitable marking material or apparatus such as a template). In the showing of FIG. 5c, one can see that the line 146 does not enter the target location 145 and, thus, it can be concluded form this image that the tissue penetrator 85 is not properly aimed at the target location 145. However, by rotating the catheter 11a in the resident blood vessel 143, to the position shown in FIG. 5d, the line 146 is caused to pass directly through the target location 145, thus indicating to the operator that the tissue penetrator 85 can now be advanced from the exit port 29a to properly penetrate from the resident vessel 143 into the target location 145, as desired.

Figure 5F:
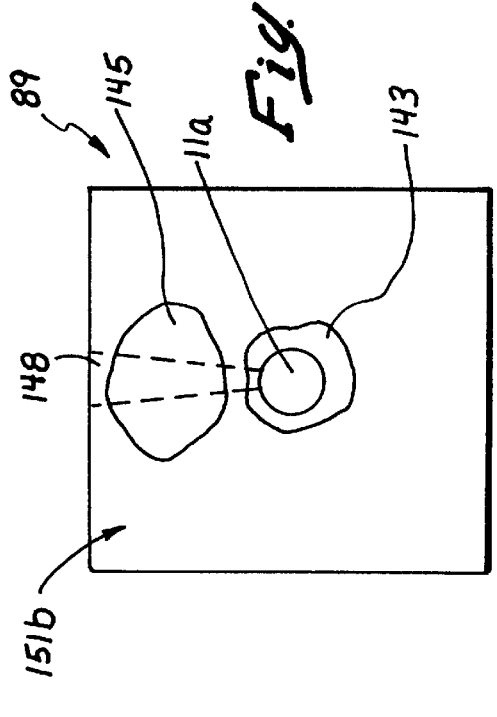
FIGS. 5e and 5f are elevational views of the screen of an imaging apparatus displaying an image from a fixed-transducer catheter as in FIG. 4 wherein the penetrator-path-indicating element(s) of the imaging transducer is/are electronically modified to produce an image that is i) visually distinct from the images produced by the other elements of the transducer array, or ii) modified to produce multiple lines that define a path region, and illustrating the manner in which the visually distinct image of the penetrator-path-indicating transducer can be used to facilitate rotational orientation of the catheter within the resident blood vessel such that the penetrator-path-indicating transducer element (and hence the penetrator) are aimed at the target location or conversely, the path region incorporates the target location within its scope.
Figure 5E:
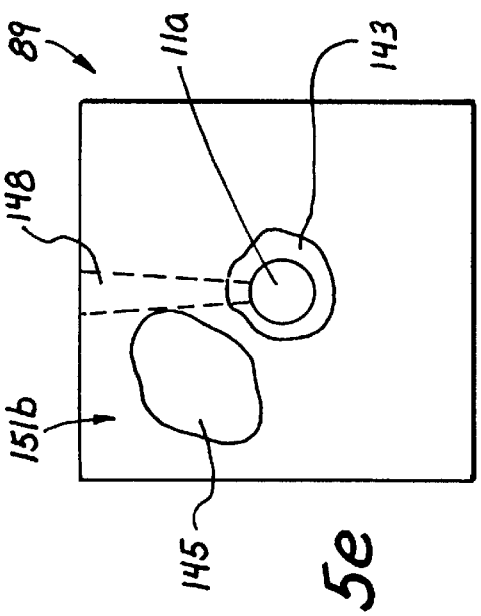

FIGS. 5e and 5f show an image 151b of the catheter 11a (FIG. 4) in the resident blood vessel 143 in which that catheter is positioned, as well as an image of the target location 145, shown here as another blood vessel. The penetrator path indicating element 121pp of the phased array transducer 81b has, in this case, been modified to provide an image that is enhanced or otherwise visually discernible from the images produced by the other transducer elements 121b of the array. In this manner, a penetrator path region 148 is visible on the screen 89 in the region that is imaged by the penetrator path indicating element 121pp. Thus, the penetrator path region 148 serves as a visual indicator of the path that will be followed by the tissue penetrator 85 as it is advanced from the catheter 11a. It will be appreciated by those of skill in the art that this penetrator path region 148 may be created by causing the penetrator path transducer element 121pp to receive more power than the other transducer elements 121b or by otherwise modifying or processing the signal received from that penetrator path indicating transducer element 121pp. In the showing of FIG. 5e, one can see that the target 145 is not encompassed by the penetrator path region 148 and, thus, it can be concluded from this image that the tissue penetrator 85 is not within acceptable range of the target location 145. However, by rotating the catheter 11a in the resident blood vessel 143, to the position shown in FIG. 5f, the target 145 is brought within an appropriate range of the penetrator path region 148, thus indicating to the operator that the tissue penetrator 85 can now be advanced from the exit port 29a to properly penetrate from the resident vessel 143 into the target location 145, as desired. Additionally, it is to be understood that the penetrator path indicating transducer element 121pp or the output on the imaging console may be additionally modified to allow imaging or project images of only that region within a predetermined distance (e,g, up to 3 mm) of the resident vessel 143 thereby signalling to the operator the possible target locations that are out of the intended range of the tissue penetrator 85 or subsequent systems or devices that may be employed to complete the intended procedure.

As an alternative to creating a penetrator path region by increasing the power transmitted to the penetrator path element transducer(s), it will be appreciated that this region 148 may be created on the imaging screen 89 electronically (e.g., as an illuminated or colored sector on the image) or it may be physically marked on the screen 89 (e.g., by felt tipped marker or other suitable marking material or apparatus such as a template). In addition, the penetrator path region may be defined by the enhancement (e.g. electronic illumination, marker or template) of two lines such as that depicted by line 146, modified to define boundries to the region 148 within which is defined an acceptable range of penetration zone.

It will be appreciated that the electronically enhanced penetrator path indicating transducer 121pp may be used in conjunction with the hash marks 300a, 300b, 300c, and 300d shown in FIGS. 5a–5b and/or the line 146 shown in FIGS. 5c and 5d, thereby enabling the operator to utilize multiple indicia to determine the appropriateness of the size and distance range of the target location 145 before advancing the tissue penetrator 85. In this way, the operator is provided with a range of acceptable accuracy depending on the desired result and taking into account what procedures may be performed subsequently (i.e. placement of a connection device or other catheter devices).

C. Examples of Methods and Procedures

The catheters 11 and 11a may be used in the performance of various revascularization procedures including, as described in detail herebelow, a Percutaneous In Situ CoronaryArtery Bypass (PICAB) procedure as well as a Percutaneous In Situ CoronaryVenous Arterialization (PICVA) procedure. It will be appreciated that, in addition to the particular PICAB and PICVA examples described in detail herebelow, the catheter system of the present invention may also be useable to perform various other procedures such as directed drug delivery procedures of the type described in co-pending U.S. patent application Ser. No. 09/048,147 and other revascularization procedures.

i. A Preferred Method for Performing the PICVA Procedure

The PICVA procedure is useable to effectively provide arterial perfusion of an ischemic region of myocardium, even in cases where a coronary artery is so extensively obstructed that no patent distal portion of the artery remains available to carry bypassed arterial; flow.

Figure 7A:
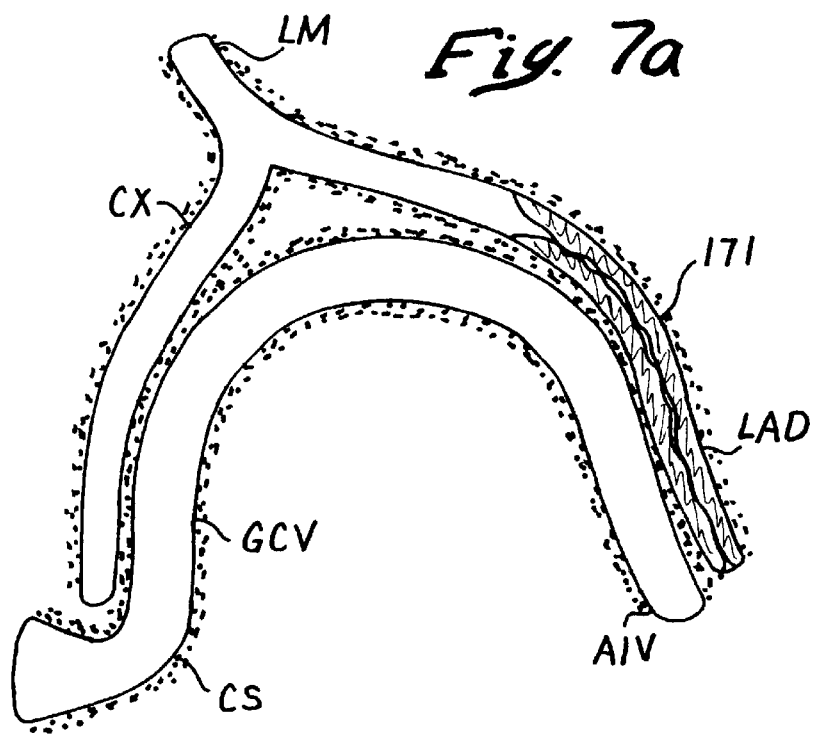
FIGS. 7a–8d illustrate the triangle of Brock-Moscheau (a name given to the formation bounded by the relationship between the arterial and venous system on the heart) and show by way of example as preferred method that can be carried out in accordance with the teachings of this invention.

FIG. 7a is a diagram of a portion of the coronary vasculature known as known as the Triangle of Brouck- Moscheau. The Triangle of Brock-Moscheau is defined by the left anterior descending coronary artery LAD, the circumflex coronary artery CX, the anterior inter ventricular vein AIV. The arteries CX and LAD are both joined to and receive blood from the left main artery. The great coronary vein GCV forms a downwardly opening U-shaped configuration with the legs of the U being adjacent to arteries CX and LAD. Obstructions resulting from a build up of plaque may be found in either or both of the arteries CX and LAD. For example and for purposes of illustrating a preferred embodiment of the method of this invention, FIG. 7a shows an obstruction 171 in the left anterior descending artery LAD.

Figure 7B:
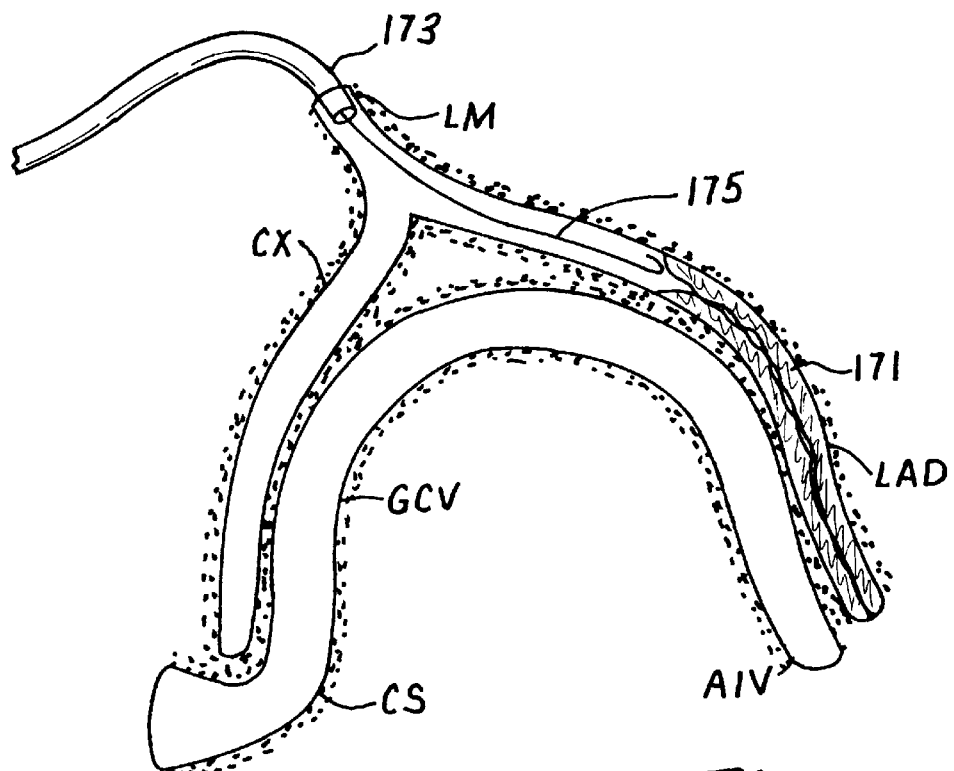

In the first step of the procedure, shown in FIG. 7b, a coronary guide catheter 173 is advanced into the left coronary ostium and a guidewire 175 such as a 0.014 inch guidewire is advanced through the guide catheter 173 into the lumen 176 of the left anterior descending artery (LAD) to a location just proximal of the obstruction 171 as shown in FIG. 7b.

Figure 7C:
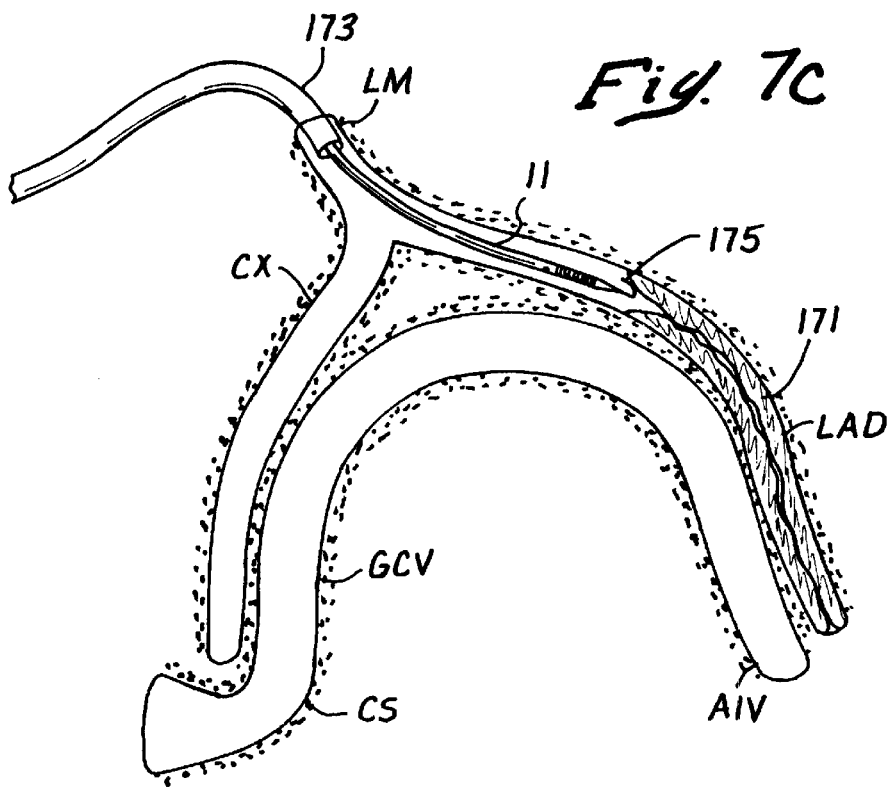
Figure 7D:
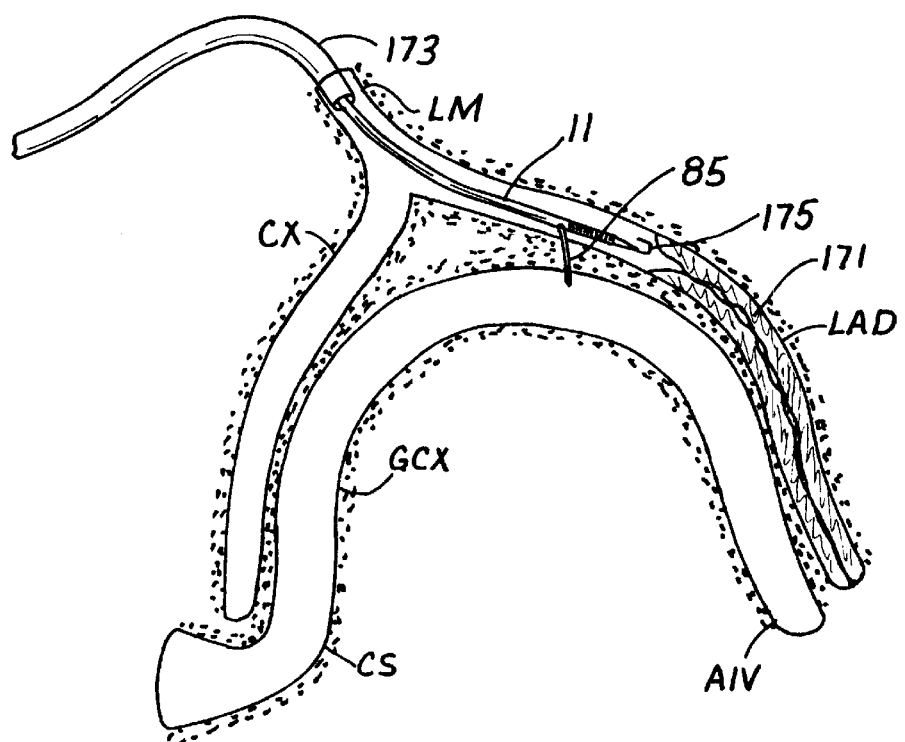

Next, as shown in FIG. 7c, the tissue penetrating catheter 11 is percutaneously inserted and transluminally advanced through the guide catheter 173 and over the guidewire 175 into the left anterior descending artery LAD to a location just proximal of the obstruction 171 (FIG. 7c). The axial position of the guidewire 175 and of the catheter 11 within the artery LAD is known by conventional techniques which may include, for example, fluoroscopy and the radiopaque marker 33. Although this procedure is described with reference to the catheter 11, it should be understood that an identical procedure would be followed for the catheter 11a. As shown in FIG. 7d, with the catheter 11 in position within the LAD, the leads 85 are coupled to the imaging console 89 and the imaging transducer 81 is actuated to obtain images as shown, by way of example, in FIG. 6a. The catheter 11 is moved, and more specifically rotated within the artery LAD until the exit port 29 and hence a penetrator path indication or path region 148 is aimed at the lumen of the vein AIV. At this point, the tissue penetrator 85 is advanced through the exit opening 29 from the catheter 11 through the walls of the artery LAD and the vein AIV and into the lumen 177 of the vein AIV upstream of the obstruction 171 as shown in FIG. 7d.

Figure 7E:
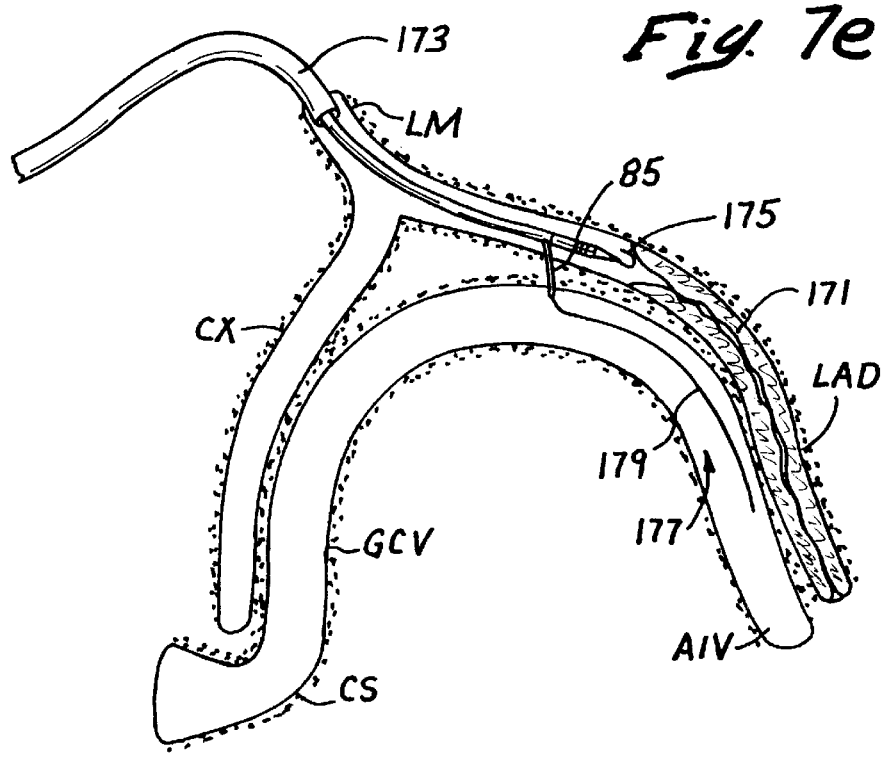

As shown in FIG. 7e, with the catheter 11 and the tissue penetrator 85 in the position shown in FIG. 7d, a first crossing guidewire 179 is advanced through the lumen 85L of the tissue penetrator 85 and into the lumen 177 of the vein AIV. The tissue penetrator 85 is then retracted into the catheter 11 leaving the crossing guidewire 179 in place such that it extends from the lumen 176 of the artery LAD into the lumen 177 of the vein AIV.

Figure 7F:
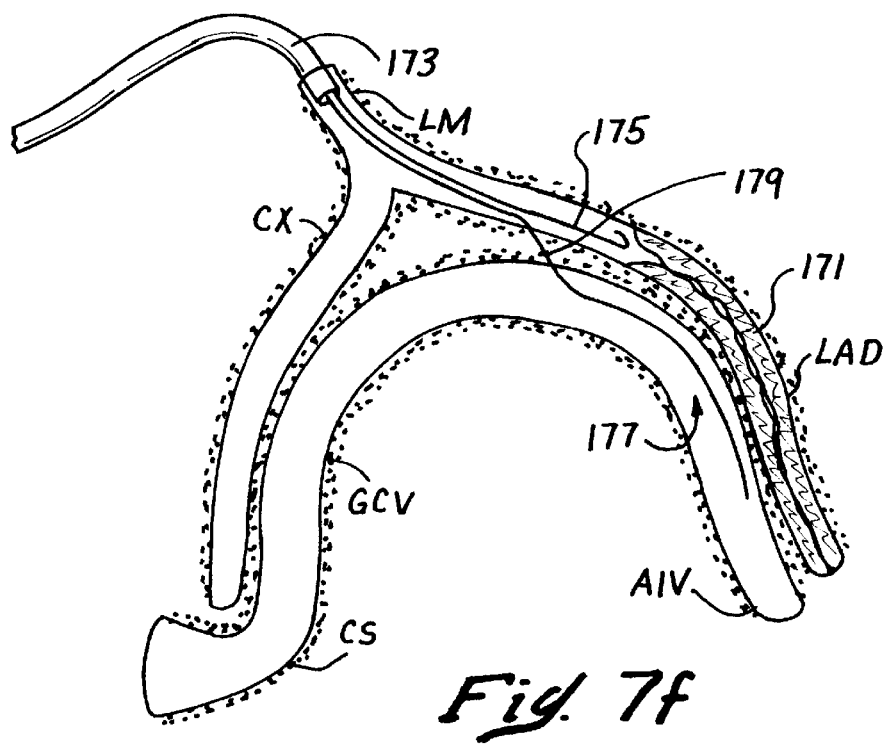

As shown in FIG. 7f, the catheter 11 is then removed by retracting it back over the guidewire 175 and out through the guide catheter 173 leaving the guidewires 175 and 179 in place.

Figure 7G:
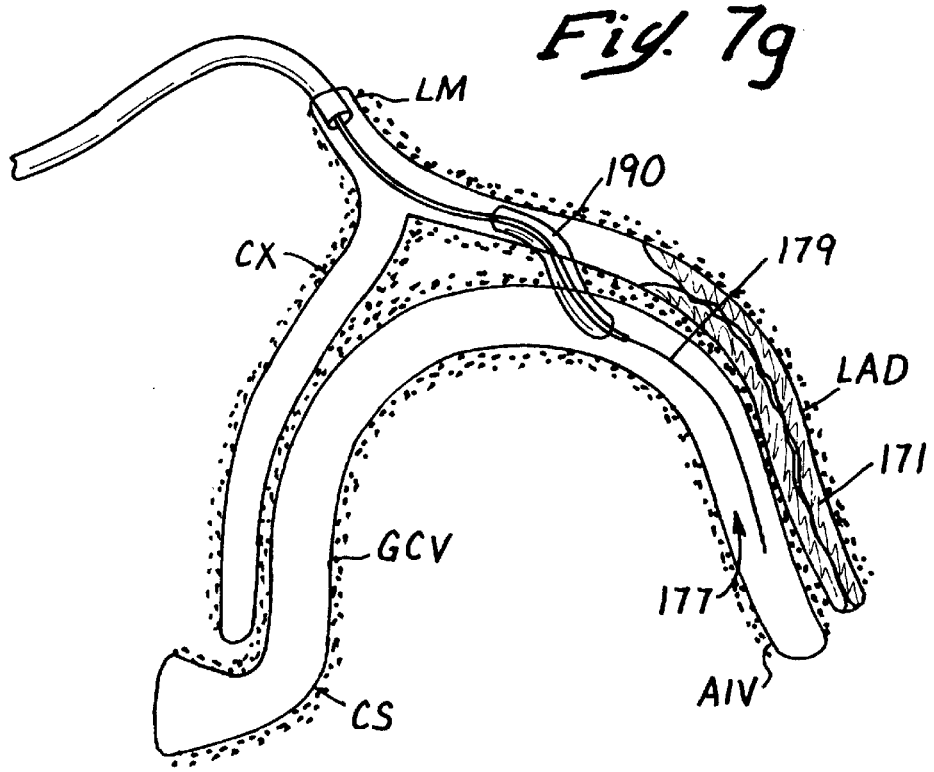

Thereafter, as shown in FIG. 7g, if it is necessary to enlarge or modify the penetration tract. created by the penetrator 85, a tract modification or enlargement apparatus 190 may be advanced over the first crossing guidewire 179 to enlarge or otherwise modify the penetration tract. This tract modifying apparatus 190 may comprise a balloon catheter or radiofrequency tissue severing device as described in U.S. patent application Ser. No. 09/056,589, the entirety of which is expressly incorporated herein by reference.

Figure 7H:
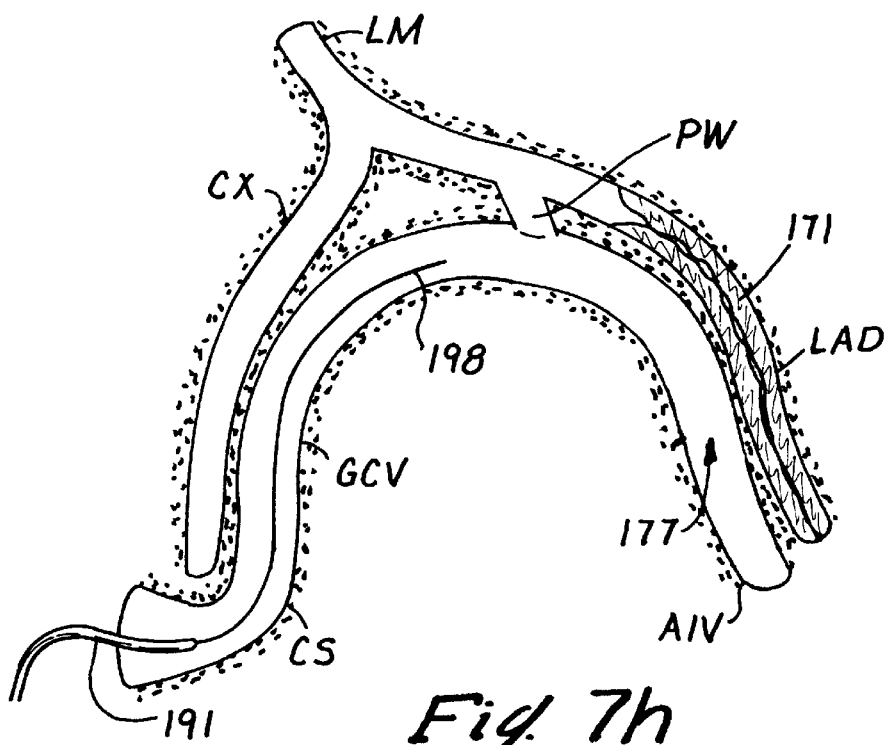

As shown in FIG. 7h, after any necessary enlargement or modification of the penetration tract has been complete, the tract modifying apparatus 190 and first crossing guidewire 179 are removed, leaving open the passageway PW between the artery LAD and vein GCV/AIV. Also, a catheter 191 is introduced into the coronary venous sinus CS and a guidewire 198 is advanced through the catheter 191 and into the vein GCV.

Figure 7I:
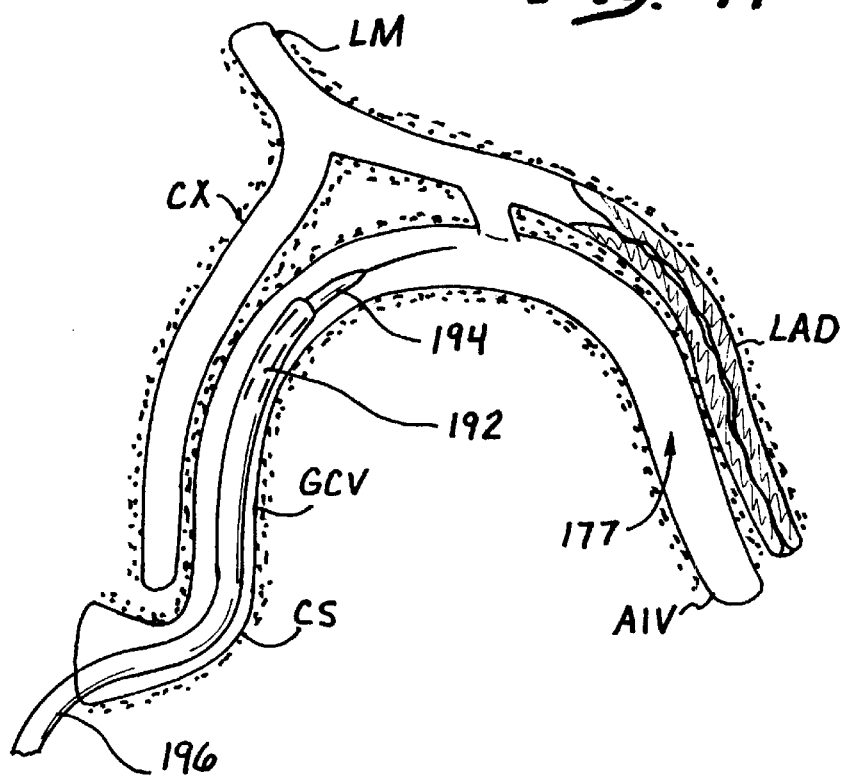

As shown in FIG. 7i, the catheter 191 is then removed and a coronary sinus guide catheter 196 is introduced over the guidewire 198 into the coronary venous sinus. A subselective sheath 192 and introducer 194 are then advanced through the coronary sinus guide catheter 191, over the guidewire 179 and into the vein GCV proximal to the passageway PW. This coronary sinus guide catheter 196, subselective sheath 192 and introducer 194 may be of the type described in detail in concurrently filed U.S. patent application Ser. No. 09/282,276 entitled CATHETERS, SYSTEMS AND METHODS FOR PERCUTANEOUS IN SITU ARTERIO-VENOUS BYPASS, the entirety of which is expressly incorporated herein by reference.

Figure 7J:
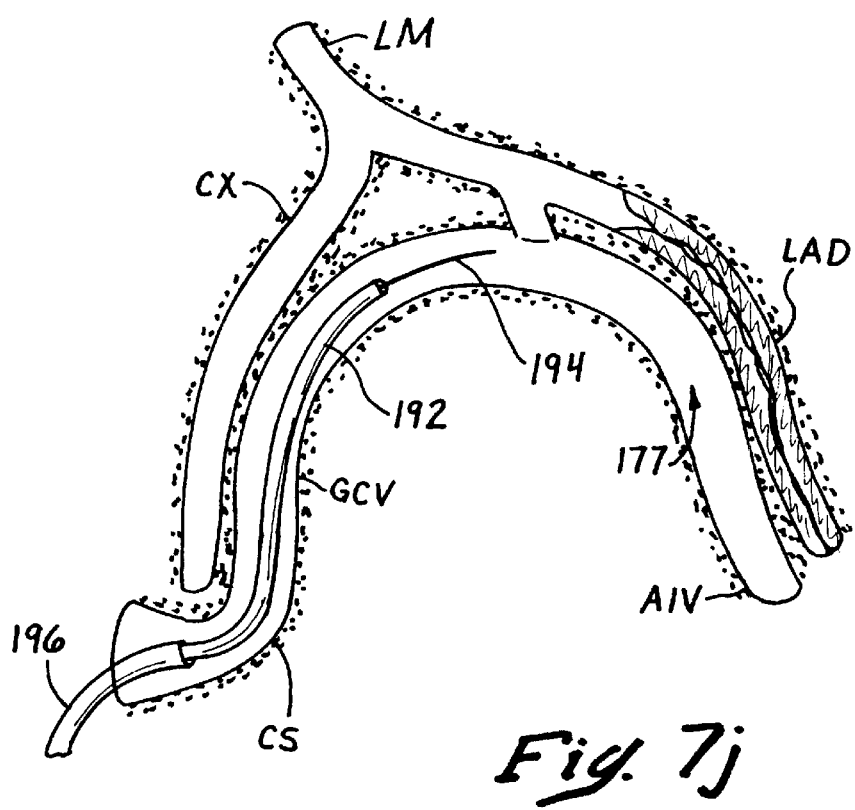

Thereafter, as shown in FIG. 7j, the introducer 194 is removed leaving the subselective sheath 192 and guidewire 194 in place.

Figure 7K:
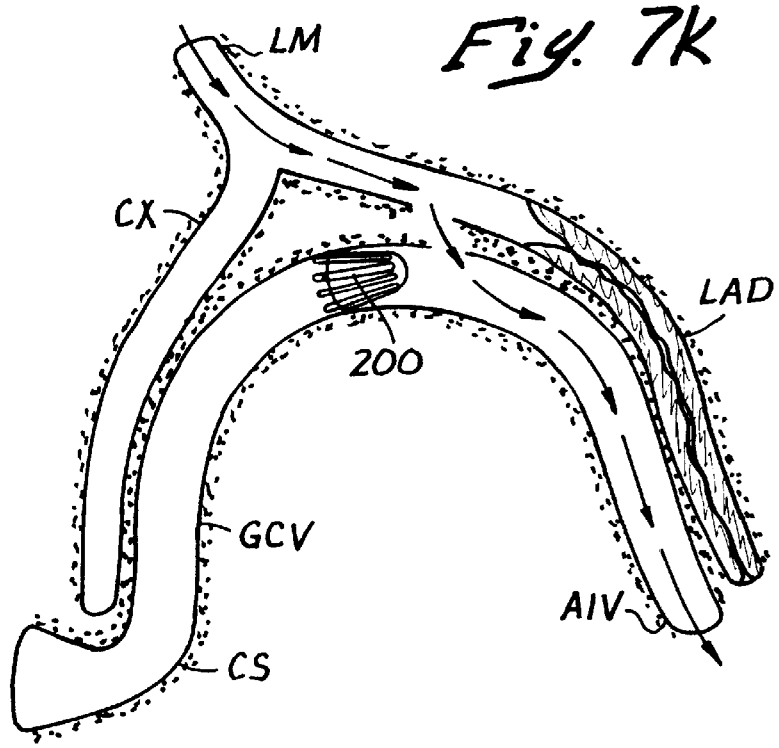

Thereafter, as shown in FIG. 7k, an embolic blocker 200 is advanced through the subselective sheath 192 and implanted in the vein GCV proximal to the passageway. This completes the PICVA procedure, allowing arterial blood to flow from the artery LAD, through the passageway PW and into the vein GCV/AIV where it flows in the direction opposite normal venous return so as to retro-perfuse the ischemic myocardium through the coronary vein(s).

i. A preferred Method for Performing the PICAB Procedure

FIGS. 8a–8d show, in step-by-step fashion, an example of the manner in which a two channel PICAB procedure may be performed, or in the alternative, how the above-described PICVA procedure (FIGS. 7a–7k) may be converted into a two-channel PICAB procedure. This PICAB procedure will typically be used in cases where the obstruction 171a does not extend into the distal LAD and thus, a patent distal LAD is available to carry blood flow to the ischemic myocarduim.

Figure 8A:
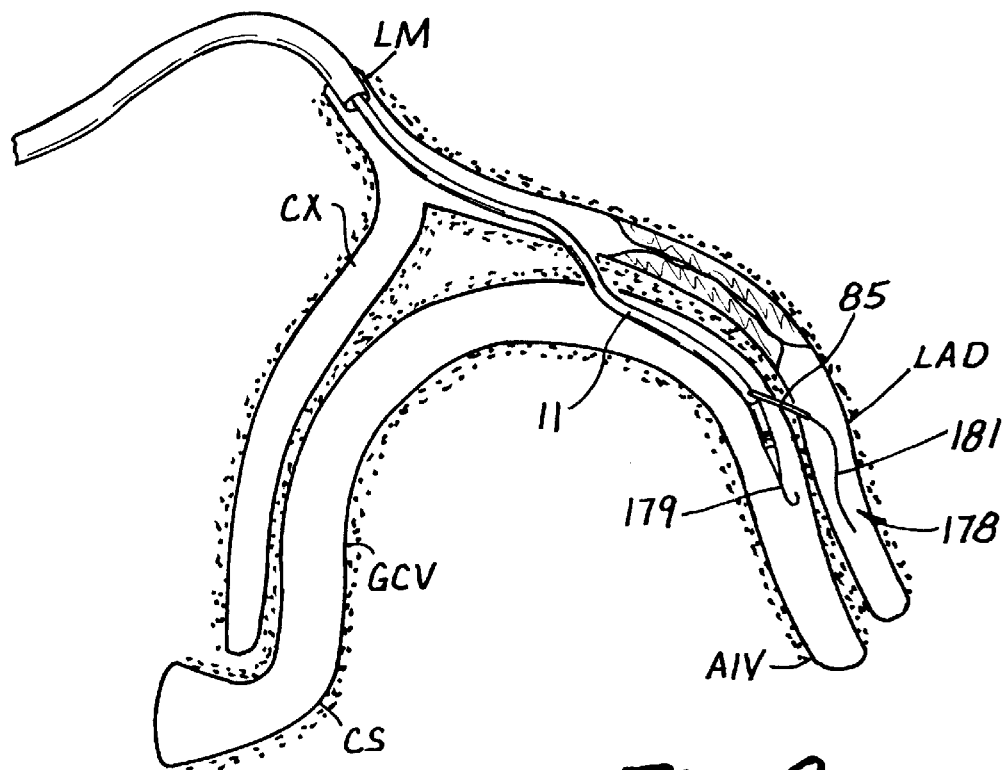

As shown in FIG. 8a, if the two channel PICAB technique is to be employed then in lieu of the placement of the embolic blocker 200 being placed (starting from the step referenced in FIG. 7g) the guidewire 175 is withdrawn and the catheter 11 is advanced over the crossing guidewire 179 to the position shown in FIG. 8a. To accomplish this, the tissue penetrator is retracted over the crossing guidewire 189 to remove the first crossing guidewire from the tissue penetrator 85 and then the crossing guidewire 179 is introduced into the main guidewire lumen 35 of the catheter 11. Consequently, the catheter 11 can be advanced overthe crossing guidewire 179 to the position of FIG. 8a wherein the catheter extends through the lumen 176 of the artery LAD, through the openings created in the walls of the artery LAD and the vein AIV and into the lumen 177 of the vein AIV. The longitudinal or axial position of the catheter 11 in the vein AIV relative to the obstruction 171 is known using conventional techniques. With the catheter 11 in the position shown in FIG. 8a, the imaging transducer 81 is again actuated and the catheter 11 is rotated within the vein AIV as required and as explained above in connection with FIGS. 6a and 6b to cause the penetrator path indication to be aimed at the lumen of the artery LAD at a location downstream of the obstruction 171. With the penetrator path indication and the exit port 29 properly aimed at the artery 171, the tissue penetrator 85 is advanced from the catheter 11 through the walls of the vein AIV and the artery LAD and into the lumen of the artery LAD as shown in FIG. 8a. Also, as shown, a second crossing guidewire 181 is advanced through the lumen 85L of the tissue penetrator 85 and into the lumen of the artery LAD.

Figure 8B:
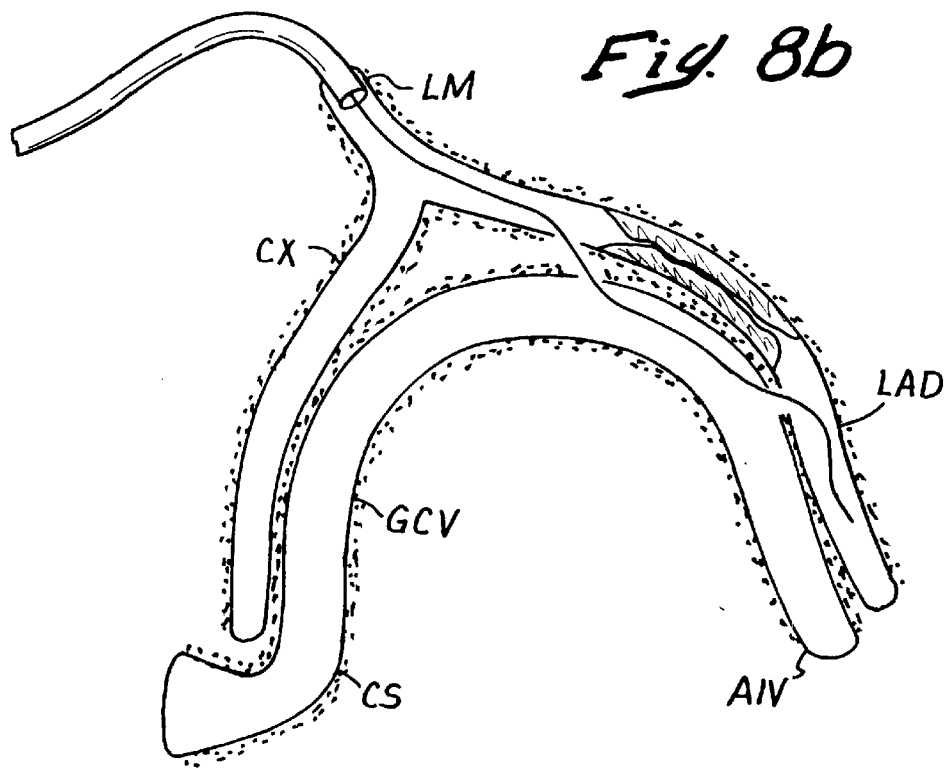

As shown in FIG. 8b, the tissue penetrator 85 is then retracted into the catheter 11 leaving the second crossing guidewire 181 in the artery LAD. The catheter 11 and the first crossing guidewire 179 are then removed leaving the second crossing guidewire 181 in place such that it extends from the artery LAD into the lumen 177 of the vein AIV and back into the artery LAD as shown in FIG. 8b.

Figure 8C:
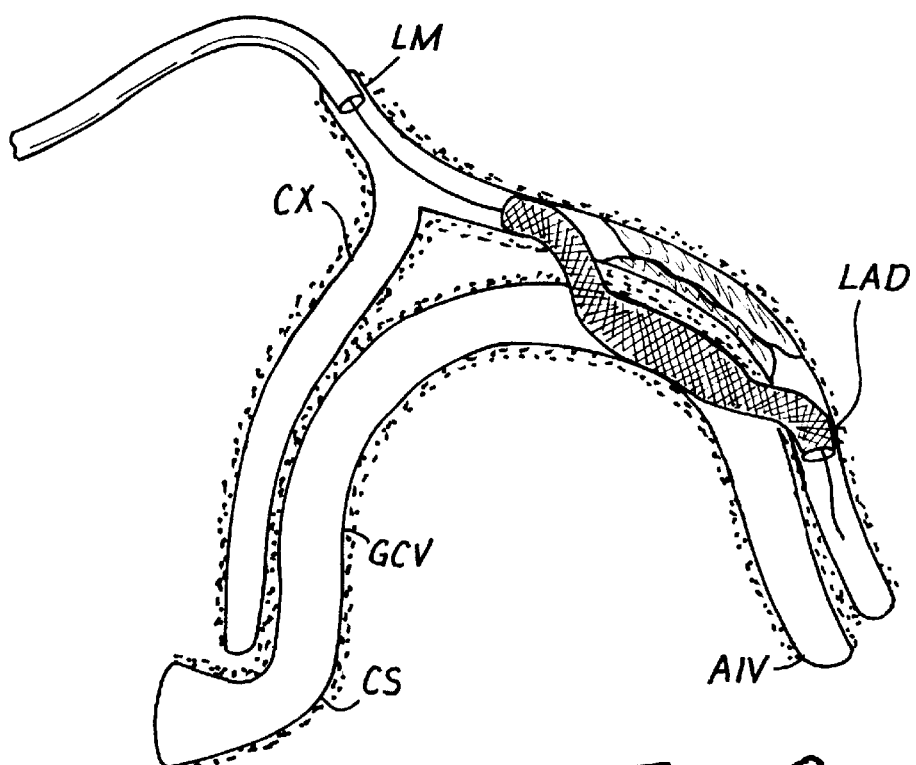
Figure 8D:
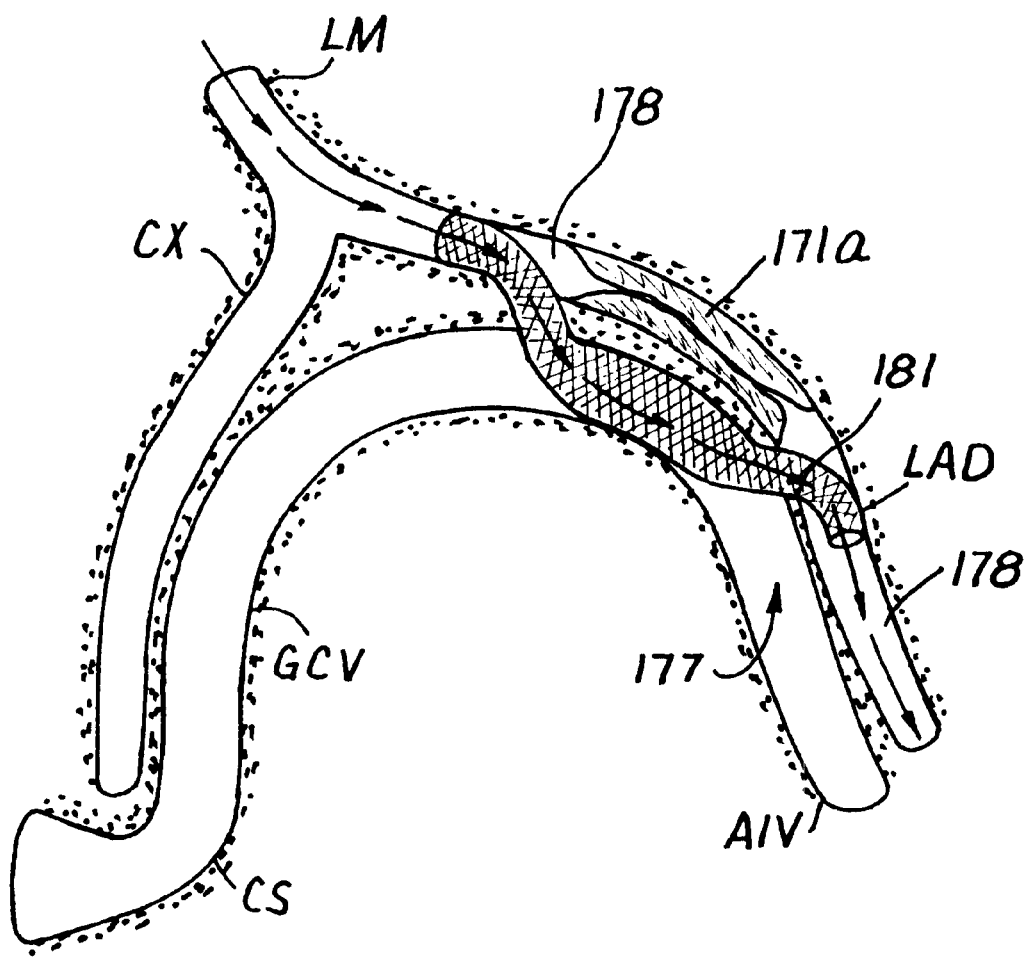

To create a blood flow channel around the obstruction 171, an expandable connector 191 may be employed. As shown in FIGS. 8c and 8d, the connector 191 is implanted such that the connector extends from the artery LAD through the openings created in the walls of the artery LAD and the vein AIV, through the lumen 177 of the vein AIV, through the openings created in the walls of the vein and artery LAD distally of the obstruction 171 and back into the artery LAD. The expandable connector may be implanted, for example, by utilizing a connector delivery catheter (not shown) and advancing such connector delivery catheter over the second crossing guidewire 181. After implantation of the connector 191, the second crossing guidewire is withdrawn and so is the guide catheter 173. It will be appreciated that instead of deploying one expandable connector, it may be preferred to employ two shorter connectors (not shown) at each of the first and second crossing sites. In this approach, a proximal and distal embolic blocker may be required to be placed in the vein proximal to the first crossing site (in the GCV) and distal to the second crossing site (in the AIV) to complete the bypass circuit.

Although exemplary embodiments of the invention have been shown and described, many changes, modifications and substitutions may be made by those having ordinary skill in the art without necessarily departing from the spirit and scope of this invention. For example, where this patent application has listed the steps of a method or procedure in a specific order, it may be possible (or even expedient in certain circumstances) to change the order in which some steps are performed, and it is intended that the particular steps of the method or procedure claims set forth herebelow not be construed as being order-specific unless such order specificity is expressly stated in the claim. Another example is that, although the specific procedures described in detail in this application may involve penetrating through an "acceptable penetration zone," such acceptable penetration zone need not be occupied by tissue but rather such acceptable penetration zone may fully or partially comprise an open space such as a body cavity or void. Accordingly, it is intended that all such additions, deletions, modifications and variations be included within the scope of the following claims.

What is claimed is:

1. A catheter device that is useable to penetrate from a position within the lumen of a first blood vessel within a patient's body in which the catheter device is positioned, through the wall of that first blood vessel and to a target location located within the patient's body outside of that first blood vessel, said catheter device comprising:
    a catheter having a proximal end and a distal end, said catheter being advanceable into said first blood vessel;
    a tissue penetrator that is advanceable from the catheter, said tissue penetrator being operative to penetrate from the lumen of the first blood vessel through the wall of that first blood vessel and to the target location;
    an imaging transducer located on or in the catheter for providing an imaging signal from which an image of at least the target location can be obtained; and,
    a marker that indicates the direction in which the tissue penetrator will advance from the catheter;
    said imaging transducer and said marker being useable in cooperation with each other to enable the operator to rotationally orient the catheter, prior to advancement of the tissue penetrator, so that the marker indicates that when the tissue penetrator is subsequently advanced from the catheter it will extend to the target location, as desired.

2. The catheter device of claim 1 wherein the imaging transducer is an ultrasound imaging transducer.

3. The catheter device of claim 2 wherein the ultrasound imaging transducer is a selected from the group consisting of:
    an annular phased array
    a rotatable transducer.

4. The catheter device of claim 3 wherein the phased array transducer is operative to image 360 degrees about the first blood vessel.

5. The catheter device of claim 1 wherein the marker includes a cage on the catheter, said cage comprises a plurality of longitudinal members disposed at circumferentially spaced apart locations about a hollow interior space, a first one of said longitudinal members being located at a circumferential position that is axially aligned with the path that will be followed by the tissue penetrator as it is advanced from the catheter.

6. The catheter device of claim 1 wherein the tissue penetrator includes a needle member formed of resilient material that is biased to a preformed curved configuration, said needle member being initially disposed in a retracted position within the catheter and subsequently advanceable from the catheter to an extended position wherein the needle member assumes its preformed curved configuration.

7. A catheter device that is useable to facilitate penetration from the lumen of a blood vessel within a patient's body in which the catheter device is positioned to a target location within the patient's body, said catheter device comprising:
    a flexible catheter having a proximal end and a distal end, said catheter being transluminally advanceable into said blood vessel;
    a tissue penetrator that is advanceable from the catheter to penetrate from the lumen of a blood vessel to a target location, provided that the catheter is rotationally oriented within the blood vessel such that the tissue penetrator is aimed at the target location;
    an imaging transducer that comprises a plurality of imaging elements fixedly mounted on the catheter to provide an imaging signal from which an image of the target location and other anatomical structures located adjacent the blood vessel can be obtained; and
    said imaging elements being mounted on the catheter at known circumferential locations relative to the path that will be followed by the tissue penetrator as the tissue penetrator advances from the catheter, said imaging transducer being thereby useable by the operator to rotationally orient the catheter such that, when the tissue penetrator is advanced from the catheter, the tissue penetrator will extend into the target location as desired.

8. A catheter device as defined in claim 7 wherein the imaging transducer is an ultrasound imaging transducer.

9. A catheter device as defined in claim 8 wherein the ultrasound imaging transducer is a phased array transducer.

10. A catheter device as defined in claim 9 wherein in the phased array transducer is operative to image 360° about the first blood vessel.

11. A catheter device as defined in claim 7 further comprising a marker which creates, on the image obtainable from the imaging, an indication of the path direction in which the penetrator will advance from the catheter.

12. A catheter device as defined in claim 11 wherein the marker comprises an imaging structure formed or mounted on the catheter, said imaging structure comprising a plurality of longitudinal members disposed at circumferentially spaced apart locations about a hollow interior space, a first one of said longitudinal members being located at a circumferential position that is aligned with the path that will be followed by the tissue penetrator as it is advanced from the catheter.

13. A catheter comprising:
   a catheter body having a proximal end, a distal end and a peripheral wall;
   said catheter of body being receivable within a blood vessel of a human patient;
   said catheter body having a penetrator lumen that terminates distally at an exit location on the peripheral wall of the catheter;
   a penetrator operatively engaged to exit from the penetrator lumen, out of the exit location, and to advance away from the catheter body on a predetermined penetrator path; and
   a phased array transducer fixedly mounted to the catheter body, said phased array transducer comprising a plurality of transducer elements positioned at circumferentially spaced apart locations, at least one of said transducer elements being in a known circumferential location relative to said exit port to provide an imaging signal from which an image of the target location and other anatomical structures located adjacent the blood vessel can be obtained to enable the operator to rotationally orient the catheter until the target location is aligned with the location of the exit port such that when the tissue penetrator is advanced from the catheter it will extend into the target location as desired.

14. A catheter as defined as in claim 13 including an imageable marker which includes a plurality of circumferentially spaced imageable members which can be sensed by the phased array transducer, said the imageable members being carried by the catheter body in a known circumferential orientation relative to the exit location so that they can be used to locate the target location and in identifying the angular orientation of the exit location.

15. A catheter as defined in claim 13 wherein the phased array transducer comprises a plurality of imaging elements arranged on the catheter body with at least one of said elements being at a known circumferential location relative to said exit location whereby said at least said one element is useable to identify the angular orientation of the exit location.

16. A catheter as defined in claim 13 wherein the catheter body is sized to be receivable in an artery of a human patient.

17. A catheter comprising:
   an elongated catheter body having a proximal end, a distal end, a guidewire lumen opening at the distal end of the catheter body and a peripheral wall, at least a distal region of said catheter body being flexible;
   said catheter body being receivable within a first blood vessel of a human patient;
   said catheter body having a penetrator lumen terminating distally at an exit location on the peripheral wall and a penetrator disposed within said lumen and advanceable out of said exit location;
   said catheter body including a major section which includes the proximal end and said exit location and a distal tip section extending from the major section to the distal end of the catheter body;
   said distal portion of the distal tip section being of smaller cross sectional area than the adjacent region of the major section; and
   an active imaging apparatus carried by the catheter body and including imaging elements the distal tip section and a lead extending proximally from said imaging elements.

18. A catheter as defined in claim 17 wherein the major section terminates distally in a distal opening and a proximal portion of the distal tip section is received in said distal opening and a distal portion of the distal tip section extends distally of said distal opening.

19. A catheter as defined in claim 18 including an imageable marker on said distal portion of the distal tip section.

20. A percutaneous, transluminal method for creating a flow channel between a first blood vessel that has a wall and a lumen and a second blood vessel that has a wall and a lumen, said method comprising the steps of:
   A. providing a catheter device that comprises:
      i. a catheter having a proximal end and a distal end, said catheter being advanceable into the lumen of the first blood vessel;
      ii. a tissue penetrator that is advanceable from the catheter, said tissue penetrator being operative to penetrate from the lumen of a first blood vessel, through the walls of the first and second blood vessels and into the lumen of a second blood vessel when the catheter is positioned and rotationally oriented within the first blood vessel such that the tissue penetrator is aimed at the second blood vessel;
      iii. an imaging transducer fixedly mounted on the catheter to provide an imaging signal from which an image of the second blood vessel and other anatomical structures located adjacent the first blood vessel can be obtained; and,
      iv. an imageable marker on the catheter to provide, on the image obtainable from the imaging signal from the imaging transducer, a penetrator path indication indicative of the path that will be followed by the tissue penetrator when the tissue penetrator is advanced from the catheter;
   B. percutaneously inserting and transluminally advancing the catheter into the first blood vessel;
   C. actuating the imaging transducer and moving the catheter within the first blood vessel until the penetrator path indication is aimed at the lumen of the second blood vessel; and,
   D. advancing the tissue penetrator from the catheter, through the walls of the first and second blood vessels and into the lumen of the second blood vessel.

21. The method of claim 20 wherein the tissue penetrator is an elongate member that has a lumen extending longitudinally therethrough and wherein said method further comprises the step of:
   E. advancing a first crossing guidewire through the lumen of the tissue penetrator and into the lumen of the second blood vessel.

22. The method of claim 21 wherein the method further comprises:
   F. retracting the tissue penetrator into the catheter leaving the first crossing guidewire in place such that it extends from the lumen of the first blood vessel into the lumen of the second blood vessel.

23. The method of claim 22 wherein the catheter device provided in Step A has a main guidewire lumen that extends longitudinally through at least a portion of the catheter and wherein the method further comprises the steps of:

I. moving the first crossing guidewire from the lumen of the tissue penetrator, and reintroducing a crossing guidewire into the main guidewire lumen of the catheter; and, H. readvancing the catheter over the first crossing guidewire to a position wherein the catheter extends through the lumen of the first blood vessel, through the openings created in the walls of the first and second blood vessels by advancement of the tissue penetrator in Step D, and into the lumen of the second blood vessel.

24. The method of claim 23 wherein the method further comprises the steps of:

I. actuating the imaging transducer and moving the catheter within the second blood vessel as required to cause the penetrator path indication to be aligned with the lumen of the first blood vessel; and J. advancing the tissue penetrator from the catheter, through the walls of the first and second blood vessels and into the lumen of the first blood vessel.

25. The method of claim 24 further comprising the step of:

K. advancing a second crossing guidewire through the lumen of the tissue penetrator and into the lumen of the first blood vessel.

26. The method of claim 25 wherein the method further comprises:

L. retracting the tissue penetrator into the catheter leaving the second crossing guidewire in place such that it extends from the lumen of the first blood vessel into the lumen of the second blood vessel and back into the lumen of the first blood vessel.

27. The method of claim 26 wherein the method further comprises the steps of:

M. providing a connector delivery catheter accompanying a radially expandable connector;

N. advancing the connector delivery catheter over the second crossing guidewire and implanting the radially expandable connector such that the connector extends from the lumen of the first blood vessel, through the openings created in the walls of the first and second blood vessels in Step D, through the lumen of the second blood vessel, through the openings created in the walls of the first and second blood vessels in Step J and back into the lumen of the first blood vessel.

28. The method of claim 24 wherein the method is carried out to bypass an obstruction in the first blood vessel and wherein the openings created in the walls of the first and second blood vessels in Step D are proximal to the obstruction and the openings created in the walls of the first and second blood vessels in Step J are distal to the obstruction.

29. A catheter device according to claim 13 wherein the phased array imaging transducer comprises an annular array of transducer elements, at least one of said transducer elements being a penetrator path indicator element that is in known spacial relationship to the path that will be followed by the tissue penetrator as the tissue penetrator is advanced from the catheter.

30. The catheter device of claim 29 further in combination with an image display screen for displaying an image received from the phased array transducer.

31. The catheter device of claim 29 wherein indicia are provided on the image display screen to distinguish between the portion of the image being received from the penetrator path indicator transducer element and those portions of the image received from the other transducer elements.

32. The catheter device of claim 31 wherein said indicia are selected from the group of indicia consisting of:

a series of hash marks that indicate the circumferential location of the image received from said penetrator path indicating element; and, a line that indicates the circumferential location of the image received from said penetrator path indicating element.

33. The catheter device of claim 31 wherein the portion of the image received from the penetrator path indicating transducer element is electronically modified to be visually discernible from the remainder of the image received from the other transducer elements.

34. A catheter device that is useable to penetrate from the lumen of a patient's blood vessel in which the catheter device is positioned to a target location within the patient's body, said catheter device comprising:

a catheter that has a proximal end and a distal end, said catheter being advanceable into said first blood vessel;

a tissue penetrator that is advanceable from the catheter, said tissue penetrator being operative to penetrate from the lumen of the blood vessel to target location provided that the catheter is rotationally oriented within the first blood vessel such that the tissue penetrator is aimed at the target location;

catheter braid being incorporated in at least a portion of said catheter body, said catheter braid having a braid angle and a pick count, the braid angle of said catheter braid being such that the pick count is less than 100 picks per inch to thereby minimize the longitudinal elongation of the catheter that may occur as the catheter is warmed from room temperature to body temperature.

35. The catheter device of claim 34 wherein the braid angle is such that the pick count is 20–30 picks per inch.

* * * * *